(12) United States Patent
Jiang

(10) Patent No.: US 6,717,034 B2
(45) Date of Patent: Apr. 6, 2004

(54) METHOD FOR MODIFYING PLANT BIOMASS

(75) Inventor: Cai-Zhong Jiang, Fremont, CA (US)

(73) Assignee: Mendel Biotechnology, Inc., Hayward, CA (US)

( * ) Notice: Subject to any disclaimer, the term of this patent is extended or adjusted under 35 U.S.C. 154(b) by 0 days.

(21) Appl. No.: 09/823,676

(22) Filed: Mar. 30, 2001

(65) Prior Publication Data

US 2003/0167537 A1 Sep. 4, 2003

(51) Int. Cl.$^7$ .......................... C12N 15/82; A01H 5/00
(52) U.S. Cl. .................. 800/290; 800/298; 435/419; 435/468
(58) Field of Search .................. 435/419, 468, 435/320.1; 800/290, 298; 536/23.6

(56) References Cited

PUBLICATIONS

GenBank Accession No. AL022604.*
Riechmann et al. Biol. Chem. 1998 vol. 379 pp. 633–646.
Martin and Paz–Ares Trends in Genetics 1997 vol. 13 pp. 67–73.
Riechmann and Meyerowitz Biol.Chem. 1997 vol 378 pp. 1079–1101.
Ishiguro and Nakamura Mol. Gen. Genet. 1994 vol. 244, pp. 563–571.
Zhang et al. Plant Cell 1992 vol 4 pp. 1575–1588.
Kim et al. Plant J. 1997 vol 11 pp. 1237–1251.
Klug and Schwabe Faseb J. 1995 vol. 9 pp. 597–604.
Burglin in Duboule (Ed.) Guidebook to the Homeobox Genes 1994 Sambrook and Tooze, OUP, Oxford UK.
Forsburg and Guarente Genes and Development 1989 vol. 3 pp. 1166–1178.
Klein et al. Mol Gen. Genet. 1996 vol 250 pp. 7–16.
Rouse et al. Science 1998 vol 279, pp. 1371–1373.
Littlewood and Evan Protein Profile 1994 vol 1. 639–709, Fold–out section.
Tucker et al. EMBO J. 1994 vol 13, pp. 2994–3002.
Foster et al FASEB J. 1994 vol 8 pp. 192–200.
de Costa eSilva et al. Plant J. 1993 vol 4 pp. 125–135.
Hall et al Plant Cell 1998 vol 10 pp. 925–936.
Aravind and Candsman Nucl. Acids Res. 1998 vol 26 pp. 4413–4421.
Stemmer Nature 1994 vol 370 pp. 389–391.
Stemmer Proc. Natl. Acad. Sci. 1994 vol 91, pp. 10747–10751.
Moore et al Proc Natl. Acad. Sci. 1998 vol 95, pp. 376–381.
Aoyama et al. Plant Cell 1995 vol 7 pp. 1773–1785.
Ma and Ptashne Cell 1987 vol 51 pp. 113–119.
Giniger and Ptashne Nature 1987 vol 330 pp. 670–672.
Bird et al Plant Mol. Biol. 1988 vol 11 pp. 651–662.
Ringli and Keller Plant Mol Biol. 1998 vol 37 , pp. 977–988.
Kaiser and Batschauer Plant Mol. Biol 1995 vol 28, pp. 231–243.
Baerson et al. Plant Mol. Biol. 1994 vol 26, pp. 1947–1959.
Ohl et al Plant cell 1990 vol 2 pp. 837–848.
Baerson and Lamppa Plant Mol. Biol. 1993 vol 22, pp. 255–267.
Van der Kop et al. Plant Mol. Biol. 1999 vol 39, pp. 979–990.
Baumann et al. Plant Cell 1999 vol 11 pp. 323–333.
Guevara–Garcia,et al. Plant Mol. Biol. 1998 vol 38 , pp. 743–753.
Shi and Olszewski Plant Mol. Biol. 1998 vol 38, pp. 1053–1060.
Willmott et al Plant Mol. Biol. 1998 vol 38, pp. 817–825.
Ainley et al Plant Mol. Biol. 1993 vol 22, pp. 13–23.
Kuhlemeier et al. Plant Cell 1989 vol 1, pp. 471–478.
Schäffner and Sheen Plant Cell 1991 vol 3, pp. 997–1012.
Siebertz et al. Plant Cell 1989 vol 1, pp. 961–968.
Buchel et al. Plant Mol. Biol 1999 vol 40, pp. 387–396.
Manners et al. Plant Mol. Biol. 1998 vol 38, pp. 1071–1080.
Gatz Annu. Rev. Plant Physiol. Plant Mol. Biol. 1997 vol 48, pp. 89–108.
Gan and Amasino Science 1995 vol 270 pp. 1986–1988.
Odell et al Plant Physiol. 1994 vol. 106, pp. 447–458.

* cited by examiner

*Primary Examiner*—Phuong T. Bui
*Assistant Examiner*—Cynthia Collins
(74) *Attorney, Agent, or Firm*—Jeffrey M. Libby; Matthew R. Kaser

(57) ABSTRACT

Recombinant polynucleotides and methods for modifying the phenotype of a plant are provided. In particular, the phenotype that is being modified is a plant's biomass. The method comprises altering the levels of a transcription factor that is introduced into the plant or that is endogenous to the plant to obtain a plant with a larger biomass.

7 Claims, 2 Drawing Sheets

Figure 1

ClustalW Formatted Alignments

SEQUENCE LISTING

```
<160> NUMBER OF SEQ ID NOS: 8

<210> SEQ ID NO 1
<211> LENGTH: 974
<212> TYPE: DNA
<213> ORGANISM: Arabidopsis thaliana
<220> FEATURE:
<221> NAME/KEY: CDS
<222> LOCATION: (62)..(874)
<223> OTHER INFORMATION: G1073

<400> SEQUENCE: 1 cccccgacc tgcctctaca gagacctgaa gattccagaa ccccacctga tcaaaaataa      60 c atg gaa ctt aac aga tct gaa gca gac gaa gca aag gcc gag acc act    109
  Met Glu Leu Asn Arg Ser Glu Ala Asp Glu Ala Lys Ala Glu Thr Thr
  1               5                   10                  15
```

| | | |
|---|---|---|
| ccc acc ggt gga gcc acc agc tca gcc aca gcc tct ggc tct tcc tcc<br>Pro Thr Gly Gly Ala Thr Ser Ser Ala Thr Ala Ser Gly Ser Ser Ser<br>          20                        25                    30 | 157 |
| gga cgt cgt cca cgt ggt cgt cct gca ggt tcc aaa aac aaa ccc aaa<br>Gly Arg Arg Pro Arg Gly Arg Pro Ala Gly Ser Lys Asn Lys Pro Lys<br>        35                       40                    45 | 205 |
| cct ccg acg att ata act aga gat agt cct aac gtc ctt aga tca cac<br>Pro Pro Thr Ile Ile Thr Arg Asp Ser Pro Asn Val Leu Arg Ser His<br> 50                      55                      60 | 253 |
| gtt ctt gaa gtc acc tcc ggt tcg gac ata tcc gag gca gtc tcc acc<br>Val Leu Glu Val Thr Ser Gly Ser Asp Ile Ser Glu Ala Val Ser Thr<br>65                 70                      75                     80 | 301 |
| tac gcc act cgt cgc ggc tgc ggc gtt tgc att ata agc ggc acg ggt<br>Tyr Ala Thr Arg Arg Gly Cys Gly Val Cys Ile Ile Ser Gly Thr Gly<br>                  85                       90                    95 | 349 |
| gcg gtc act aac gtc acg ata cgg caa cct gcg gct ccg gct ggt gga<br>Ala Val Thr Asn Val Thr Ile Arg Gln Pro Ala Ala Pro Ala Gly Gly<br>                100                    105                  110 | 397 |
| ggt gtg att acc ctg cat ggt cgg ttt gac att ttg tct ttg acc ggt<br>Gly Val Ile Thr Leu His Gly Arg Phe Asp Ile Leu Ser Leu Thr Gly<br>                115                    120                  125 | 445 |
| act gcg ctt cca ccg cct gca cca ccg gga gca gga ggt ttg acg gtg<br>Thr Ala Leu Pro Pro Pro Ala Pro Pro Gly Ala Gly Gly Leu Thr Val<br>130                     135                    140 | 493 |
| tat cta gcc gga ggt caa gga caa gtt gta gga ggg aat gtg gct ggt<br>Tyr Leu Ala Gly Gly Gln Gly Gln Val Val Gly Gly Asn Val Ala Gly<br>145                   150                    155                  160 | 541 |
| tcg tta att gct tcg gga ccg gta gtg ttg atg gct gct tct ttt gca<br>Ser Leu Ile Ala Ser Gly Pro Val Val Leu Met Ala Ala Ser Phe Ala<br>                165                    170                  175 | 589 |
| aac gca gtt tat gat agg tta ccg att gaa gag gaa gaa acc cca ccg<br>Asn Ala Val Tyr Asp Arg Leu Pro Ile Glu Glu Glu Glu Thr Pro Pro<br>              180                    185                  190 | 637 |
| ccg aga acc acc ggg gtg cag cag cag cag ccg gag gcg tct cag tcg<br>Pro Arg Thr Thr Gly Val Gln Gln Gln Gln Pro Glu Ala Ser Gln Ser<br>                195                    200                  205 | 685 |
| tcg gag gtt acg ggg agt ggg gcc cag gcg tgt gag tca aac ctc caa<br>Ser Glu Val Thr Gly Ser Gly Ala Gln Ala Cys Glu Ser Asn Leu Gln<br>210                     215                    220 | 733 |
| ggt gga aat ggt gga gga ggt gtt gct ttc tac aat ctt gga atg aat<br>Gly Gly Asn Gly Gly Gly Gly Val Ala Phe Tyr Asn Leu Gly Met Asn<br>225                   230                    235                  240 | 781 |
| atg aac aat ttt caa ttc tcc ggg gga gat att tac ggt atg agc ggc<br>Met Asn Asn Phe Gln Phe Ser Gly Gly Asp Ile Tyr Gly Met Ser Gly<br>                245                    250                  255 | 829 |
| ggt agc gga gga ggt ggt ggc ggt gcg act aga ccc gcg ttt tag<br>Gly Ser Gly Gly Gly Gly Gly Ala Thr Arg Pro Ala Phe<br>                260                    265                  270 | 874 |
| agtttagcg ttttggtgac acctttgtt gcgtttgcgt gtttgacctc aaactactag | 934 |
| gctactagct atagcggttg cgaaatgcga atattaggtt | 974 |

<210> SEQ ID NO 2
<211> LENGTH: 270
<212> TYPE: PRT
<213> ORGANISM: Arabidopsis thaliana

<400> SEQUENCE: 2

Met Glu Leu Asn Arg Ser Glu Ala Asp Glu Ala Lys Ala Glu Thr Thr
1               5                   10                  15

-continued

| | | | | | | | | | | | |
|---|---|---|---|---|---|---|---|---|---|---|---|
|Pro|Thr|Gly|Gly|Ala|Thr|Ser|Ser|Ala|Thr|Ala|Ser|Gly|Ser|Ser|Ser|
| | | |20| | |25| | | |30| |
|Gly|Arg|Arg|Pro|Arg|Gly|Arg|Pro|Ala|Gly|Ser|Lys|Asn|Lys|Pro|Lys|
| | |35| | | |40| | | |45| |
|Pro|Pro|Thr|Ile|Ile|Thr|Arg|Asp|Ser|Pro|Asn|Val|Leu|Arg|Ser|His|
| |50| | | |55| | | |60| | |
|Val|Leu|Glu|Val|Thr|Ser|Gly|Ser|Asp|Ile|Ser|Glu|Ala|Val|Ser|Thr|
|65| | | |70| | | |75| | | |80|
|Tyr|Ala|Thr|Arg|Arg|Gly|Cys|Gly|Val|Cys|Ile|Ile|Ser|Gly|Thr|Gly|
| | | |85| | | |90| | | |95|
|Ala|Val|Thr|Asn|Val|Thr|Ile|Arg|Gln|Pro|Ala|Ala|Pro|Ala|Gly|Gly|
| | | |100| | | |105| | | |110|
|Gly|Val|Ile|Thr|Leu|His|Gly|Arg|Phe|Asp|Ile|Leu|Ser|Leu|Thr|Gly|
| | |115| | | |120| | | |125|
|Thr|Ala|Leu|Pro|Pro|Pro|Ala|Pro|Pro|Gly|Ala|Gly|Gly|Leu|Thr|Val|
| |130| | | |135| | | |140| | |
|Tyr|Leu|Ala|Gly|Gly|Gln|Gly|Gln|Val|Val|Gly|Gly|Asn|Val|Ala|Gly|
|145| | | |150| | | |155| | | |160|
|Ser|Leu|Ile|Ala|Ser|Gly|Pro|Val|Val|Leu|Met|Ala|Ala|Ser|Phe|Ala|
| | | |165| | | |170| | | |175|
|Asn|Ala|Val|Tyr|Asp|Arg|Leu|Pro|Ile|Glu|Glu|Glu|Thr|Pro|Pro|
| | |180| | | |185| | | |190| |
|Pro|Arg|Thr|Thr|Gly|Val|Gln|Gln|Gln|Pro|Glu|Ala|Ser|Gln|Ser|
| |195| | | |200| | | |205| |
|Ser|Glu|Val|Thr|Gly|Ser|Gly|Ala|Gln|Ala|Cys|Glu|Ser|Asn|Leu|Gln|
| |210| | | |215| | | |220| |
|Gly|Gly|Asn|Gly|Gly|Gly|Gly|Val|Ala|Phe|Tyr|Asn|Leu|Gly|Met|Asn|
|225| | | |230| | | |235| | | |240|
|Met|Asn|Asn|Phe|Gln|Phe|Ser|Gly|Gly|Asp|Ile|Tyr|Gly|Met|Ser|Gly|
| | | |245| | | |250| | | |255|
|Gly|Ser|Gly|Gly|Gly|Gly|Gly|Gly|Ala|Thr|Arg|Pro|Ala|Phe|
| | |260| | | |265| | | |270|

```
<210> SEQ ID NO 3
<211> LENGTH: 1040
<212> TYPE: DNA
<213> ORGANISM: Arabidopsis thaliana
<220> FEATURE:
<221> NAME/KEY: CDS
<222> LOCATION: (82)..(879)
<223> OTHER INFORMATION: G2789

<400> SEQUENCE: 3
ctttagggac accaaatcta ttcaacctaa agccttctt  ttccctata ttgaccaact      60 ttttagcgaa tcagaagagg a atg gat gag gta tct cgt tct cat aca ccg     111
                        Met Asp Glu Val Ser Arg Ser His Thr Pro
                         1               5                  10 caa ttt cta tca agt gat cat cag cac tat cac cat caa aac gct gga    159
Gln Phe Leu Ser Ser Asp His Gln His Tyr His His Gln Asn Ala Gly
            15                  20                  25 cga caa aaa cgc ggc aga gaa gaa gaa gga gtt gaa ccc aac aat ata    207
Arg Gln Lys Arg Gly Arg Glu Glu Glu Gly Val Glu Pro Asn Asn Ile
        30                  35                  40 ggg gaa gac cta gcc acc ttt cct tcc gga gaa gag aat atc aag aag    255
Gly Glu Asp Leu Ala Thr Phe Pro Ser Gly Glu Glu Asn Ile Lys Lys
    45                  50                  55 aga agg cca cgt ggc aga cct gct ggt tcc aag aac aaa ccc aaa gca    303
```

```
                                                                          -continued Arg Arg Pro Arg Gly Arg Pro Ala Gly Ser Lys Asn Lys Pro Lys Ala
         60                  65                  70 cca atc ata gtc act cgc gac tcc gcg aac gcc ttc aga tgt cac gtc      351
Pro Ile Ile Val Thr Arg Asp Ser Ala Asn Ala Phe Arg Cys His Val
 75                  80                  85                  90 atg gag ata acc aac gcc tgc gat gta atg gaa agc cta gcc gtc ttc      399
Met Glu Ile Thr Asn Ala Cys Asp Val Met Glu Ser Leu Ala Val Phe
                 95                 100                 105 gct aga cgc cgt cag cgt ggc gtt tgc gtc ttg acc gga aac ggg gcc      447
Ala Arg Arg Arg Gln Arg Gly Val Cys Val Leu Thr Gly Asn Gly Ala
            110                 115                 120 gtt aca aac gtc acc gtt aga caa cct ggc gga ggc gtc gtc agt tta      495
Val Thr Asn Val Thr Val Arg Gln Pro Gly Gly Gly Val Val Ser Leu
        125                 130                 135 cac gga cgg ttt gag att ctt tct ctc tcg ggt tcg ttt ctt cct cca      543
His Gly Arg Phe Glu Ile Leu Ser Leu Ser Gly Ser Phe Leu Pro Pro
    140                 145                 150 ccg gca cca cca gct gcg tct ggt tta aag gtt tac tta gcc ggt ggt      591
Pro Ala Pro Pro Ala Ala Ser Gly Leu Lys Val Tyr Leu Ala Gly Gly
155                 160                 165                 170 caa ggt caa gtg atc gga ggc agt gtg gtg gga ccg ctt acg gca tca      639
Gln Gly Gln Val Ile Gly Gly Ser Val Val Gly Pro Leu Thr Ala Ser
                175                 180                 185 agt ccg gtg gtc gtt atg gca gct tca ttt gga aac gca tct tac gag      687
Ser Pro Val Val Val Met Ala Ala Ser Phe Gly Asn Ala Ser Tyr Glu
            190                 195                 200 agg ctg cca cta gag gag gag gag gaa act gaa aga gaa ata gat gga      735
Arg Leu Pro Leu Glu Glu Glu Glu Glu Thr Glu Arg Glu Ile Asp Gly
        205                 210                 215 aac gcg gct agg gcg att gga acg caa acg cag aaa cag tta atg caa      783
Asn Ala Ala Arg Ala Ile Gly Thr Gln Thr Gln Lys Gln Leu Met Gln
    220                 225                 230 gat gcg aca tcg ttt att ggg tcg ccg tcg aat tta att aac tct gtt      831
Asp Ala Thr Ser Phe Ile Gly Ser Pro Ser Asn Leu Ile Asn Ser Val
235                 240                 245                 250 tcg ttg cca ggt gaa gct tat tgg gga acg caa cga ccg tct ttc taa      879
Ser Leu Pro Gly Glu Ala Tyr Trp Gly Thr Gln Arg Pro Ser Phe
                255                 260                 265 gataatatca ttgataatat aagtttcgtc ttcttattct ttttcacttt ttaccttttt      939
cactttctta ggttttgttt taacgtttga ttaatacctg aaggttttg gaaaattttc      999 gatcggataa aaggatttat gttgcgagcc gaaacgcggc c                        1040

<210> SEQ ID NO 4
<211> LENGTH: 265
<212> TYPE: PRT
<213> ORGANISM: Arabidopsis thaliana

<400> SEQUENCE: 4

Met Asp Glu Val Ser Arg Ser His Thr Pro Gln Phe Leu Ser Asp
 1               5                  10                  15

His Gln His Tyr His His Gln Asn Ala Gly Arg Gln Lys Arg Gly Arg
                 20                  25                  30

Glu Glu Glu Gly Val Glu Pro Asn Asn Ile Gly Glu Asp Leu Ala Thr
            35                  40                  45

Phe Pro Ser Gly Glu Glu Asn Ile Lys Lys Arg Arg Pro Arg Gly Arg
        50                  55                  60

Pro Ala Gly Ser Lys Asn Lys Pro Lys Ala Pro Ile Ile Val Thr Arg
65                  70                  75                  80
```

```
Asp Ser Ala Asn Ala Phe Arg Cys His Val Met Glu Ile Thr Asn Ala
                 85                  90                  95
Cys Asp Val Met Glu Ser Leu Ala Val Phe Ala Arg Arg Gln Arg
            100                 105                 110
Gly Val Cys Val Leu Thr Gly Asn Gly Ala Val Thr Asn Val Thr Val
            115                 120                 125
Arg Gln Pro Gly Gly Val Val Ser Leu His Gly Arg Phe Glu Ile
130                 135                 140
Leu Ser Leu Ser Gly Ser Phe Leu Pro Pro Ala Pro Pro Ala Ala
145                 150                 155                 160
Ser Gly Leu Lys Val Tyr Leu Ala Gly Gln Gly Gln Val Ile Gly
                165                 170                 175
Gly Ser Val Val Gly Pro Leu Thr Ala Ser Ser Pro Val Val Met
            180                 185                 190
Ala Ala Ser Phe Gly Asn Ala Ser Tyr Glu Arg Leu Pro Leu Glu Glu
            195                 200                 205
Glu Glu Glu Thr Glu Arg Glu Ile Asp Gly Asn Ala Ala Arg Ala Ile
        210                 215                 220
Gly Thr Gln Thr Gln Lys Gln Leu Met Gln Asp Ala Thr Ser Phe Ile
225                 230                 235                 240
Gly Ser Pro Ser Asn Leu Ile Asn Ser Val Ser Leu Pro Gly Glu Ala
                245                 250                 255
Tyr Trp Gly Thr Gln Arg Pro Ser Phe
            260                 265

<210> SEQ ID NO 5
<211> LENGTH: 1130
<212> TYPE: DNA
<213> ORGANISM: Arabidopsis thaliana
<220> FEATURE:
<221> NAME/KEY: CDS
<222> LOCATION: (189)..(1019)
<223> OTHER INFORMATION: G1945

<400> SEQUENCE: 5
atttcccaaa gggatttacg aaaagtccct ctcctctatc atctctttat tcaccccata      60
ccaacaacct ctacatcttc ttcttcttct tcctcctctt ttattttctt tttaaatcat     120
ttacacaaaa atccaaagac aaatctgaaa tctctaataa acaaatccat aaaataagaa     180 aaacaaag atg aaa ggt gaa tac aga gag caa aag agt aac gaa atg ttt     230
         Met Lys Gly Glu Tyr Arg Glu Gln Lys Ser Asn Glu Met Phe
         1               5                  10 tcc aag ctt cct cat cat caa caa caa cag caa caa caa caa caa caa     278
Ser Lys Leu Pro His His Gln Gln Gln Gln Gln Gln Gln Gln Gln Gln
15                  20                  25                  30 cac tct ctt acc tct cac ttc cac ctc tcc tcc acc gta acc ccc acc     326
His Ser Leu Thr Ser His Phe His Leu Ser Ser Thr Val Thr Pro Thr
                35                  40                  45 gtc gat gac tcc tcc atc gaa gtg gtc cga cgt cca cgt ggc aga cca     374
Val Asp Asp Ser Ser Ile Glu Val Val Arg Arg Pro Arg Gly Arg Pro
            50                  55                  60 cca ggt tcc aaa aac aaa cct aaa cca ccc gtc ttc gtc aca cgt gac     422
Pro Gly Ser Lys Asn Lys Pro Lys Pro Pro Val Phe Val Thr Arg Asp
65                  70                  75 acc gac cct cct atg agt cct tac atc ctc gaa gtt cct tca gga aac     470
Thr Asp Pro Pro Met Ser Pro Tyr Ile Leu Glu Val Pro Ser Gly Asn
    80                  85                  90
```

```
gac gtc gtc gaa gcc atc aac cgt ttc tgc cgc cgt aaa tcc atc gga    518
Asp Val Val Glu Ala Ile Asn Arg Phe Cys Arg Arg Lys Ser Ile Gly
 95                 100                 105                 110 gtc tgc gtc ctt agt ggc tct ggc tct gta gct aac gtc act tta cgt    566
Val Cys Val Leu Ser Gly Ser Gly Ser Val Ala Asn Val Thr Leu Arg
             115                 120                 125 cag cca tca ccg gca gct ctt ggc tct acc ata act ttc cat gga aag    614
Gln Pro Ser Pro Ala Ala Leu Gly Ser Thr Ile Thr Phe His Gly Lys
         130                 135                 140 ttt gat ctc ctc tcc gtc tcc gca acg ttt ctc cct cct ccg cct cgt    662
Phe Asp Leu Leu Ser Val Ser Ala Thr Phe Leu Pro Pro Pro Pro Arg
     145                 150                 155 act tcc ttg tct cct ccc gtt tct aac ttc ttc acc gtc tct ctc gct    710
Thr Ser Leu Ser Pro Pro Val Ser Asn Phe Phe Thr Val Ser Leu Ala
 160                 165                 170 gga cct caa gga caa atc atc gga ggg ttc gtc gct ggt cca ctt att    758
Gly Pro Gln Gly Gln Ile Ile Gly Gly Phe Val Ala Gly Pro Leu Ile
175                 180                 185                 190 tcg gca gga aca gtt tac gtc atc gcc gca agt ttc aac aac cct tct    806
Ser Ala Gly Thr Val Tyr Val Ile Ala Ala Ser Phe Asn Asn Pro Ser
             195                 200                 205 tat cac cgg tta ccg gcg gaa gaa gag caa aaa cac tcg gcg ggg aca    854
Tyr His Arg Leu Pro Ala Glu Glu Glu Gln Lys His Ser Ala Gly Thr
         210                 215                 220 ggg gaa aga gag gga caa tct ccg ccg gtc tct ggt ggc ggt gaa gag    902
Gly Glu Arg Glu Gly Gln Ser Pro Pro Val Ser Gly Gly Gly Glu Glu
     225                 230                 235 tca gga cag atg gcg gga agt gga gga gag tcg tgt ggg gta tca atg    950
Ser Gly Gln Met Ala Gly Ser Gly Gly Glu Ser Cys Gly Val Ser Met
 240                 245                 250 tac agt tgc cac atg ggt ggc tct gat gtt att tgg gcc cct aca gcc    998
Tyr Ser Cys His Met Gly Gly Ser Asp Val Ile Trp Ala Pro Thr Ala
255                 260                 265                 270 aga gct cca ccg cca tac taa ccaatccttc tttcacaaat ctctttcttt      1049
Arg Ala Pro Pro Pro Tyr
             275 cttttttgt tttttttgt tttgggttag gatgaatcaa gaaactaggg tttttttttt   1109 tttttttaa aaaaaaaaa a                                             1130

<210> SEQ ID NO 6
<211> LENGTH: 276
<212> TYPE: PRT
<213> ORGANISM: Arabidopsis thaliana

<400> SEQUENCE: 6

Met Lys Gly Glu Tyr Arg Glu Gln Lys Ser Asn Glu Met Phe Ser Lys
 1               5                  10                  15

Leu Pro His His Gln Gln Gln Gln Gln Gln Gln Gln Gln His Ser
             20                  25                  30

Leu Thr Ser His Phe His Leu Ser Ser Val Thr Pro Thr Val Asp
         35                  40                  45

Asp Ser Ser Ile Glu Val Val Arg Pro Arg Gly Arg Pro Gly
     50                  55                  60

Ser Lys Asn Lys Pro Lys Pro Pro Val Phe Val Thr Arg Asp Thr Asp
 65                  70                  75                  80

Pro Pro Met Ser Pro Tyr Ile Leu Glu Val Pro Ser Gly Asn Asp Val
                 85                  90                  95

Val Glu Ala Ile Asn Arg Phe Cys Arg Arg Lys Ser Ile Gly Val Cys
```

```
                    100                 105                 110
Val Leu Ser Gly Ser Gly Ser Val Ala Asn Val Thr Leu Arg Gln Pro
            115                 120                 125

Ser Pro Ala Ala Leu Gly Ser Thr Ile Thr Phe His Gly Lys Phe Asp
        130                 135                 140

Leu Leu Ser Val Ser Ala Thr Phe Leu Pro Pro Pro Arg Thr Ser
145                 150                 155                 160

Leu Ser Pro Pro Val Ser Asn Phe Phe Thr Val Ser Leu Ala Gly Pro
                165                 170                 175

Gln Gly Gln Ile Ile Gly Gly Phe Val Ala Gly Pro Leu Ile Ser Ala
            180                 185                 190

Gly Thr Val Tyr Val Ile Ala Ala Ser Phe Asn Asn Pro Ser Tyr His
        195                 200                 205

Arg Leu Pro Ala Glu Glu Gln Lys His Ser Ala Gly Thr Gly Glu
    210                 215                 220

Arg Glu Gly Gln Ser Pro Val Ser Gly Gly Glu Ser Gly
225                 230                 235                 240

Gln Met Ala Gly Ser Gly Glu Ser Cys Gly Val Ser Met Tyr Ser
                245                 250                 255

Cys His Met Gly Gly Ser Asp Val Ile Trp Ala Pro Thr Ala Arg Ala
            260                 265                 270

Pro Pro Pro Tyr
        275

<210> SEQ ID NO 7
<211> LENGTH: 1050
<212> TYPE: DNA
<213> ORGANISM: Arabidopsis thaliana
<220> FEATURE:
<221> NAME/KEY: CDS
<222> LOCATION: (63)..(740)
<223> OTHER INFORMATION: G2155

<400> SEQUENCE: 7
ctcatatata ccaaccaaac ctctctctgc atctttatta acacaaaatt ccaaaagatt      60 aa atg ttg tcg aag ctc cct aca cag cga cac ttg cac ctc tct ccc       107
   Met Leu Ser Lys Leu Pro Thr Gln Arg His Leu His Leu Ser Pro
    1               5                   10                  15 tcc tct ccc tcc atg gaa acc gtc ggg cgt cca cgt ggc aga cct cga     155
Ser Ser Pro Ser Met Glu Thr Val Gly Arg Pro Arg Gly Arg Pro Arg
            20                  25                  30 ggt tcc aaa aac aaa cct aaa gct cca atc ttt gtc acc att gac cct     203
Gly Ser Lys Asn Lys Pro Lys Ala Pro Ile Phe Val Thr Ile Asp Pro
        35                  40                  45 cct atg agt cct tac atc ctc gaa gtg cca tcc gga aac gat gtc gtt     251
Pro Met Ser Pro Tyr Ile Leu Glu Val Pro Ser Gly Asn Asp Val Val
    50                  55                  60 gaa gcc cta aac cgt ttc tgc cgc ggt aaa gcc atc ggc ttt tgc gtc     299
Glu Ala Leu Asn Arg Phe Cys Arg Gly Lys Ala Ile Gly Phe Cys Val
65                  70                  75 ctc agt ggc tca ggc tcc gtt gct gat gtc act ttg cgt cag cct tct     347
Leu Ser Gly Ser Gly Ser Val Ala Asp Val Thr Leu Arg Gln Pro Ser
80                  85                  90                  95 ccg gca gct cct ggc tca acc att act ttc cac gga aag ttc gat ctt     395
Pro Ala Ala Pro Gly Ser Thr Ile Thr Phe His Gly Lys Phe Asp Leu
                100                 105                 110 ctc tct gtc tcc gcc act ttc ctc cct cct cta cct cct acc tcc ttg     443
Leu Ser Val Ser Ala Thr Phe Leu Pro Pro Leu Pro Pro Thr Ser Leu
```

| | | | | | | | | | | | | | | | | |
|---|---|---|---|---|---|---|---|---|---|---|---|---|---|---|---|---|
| | | | 115 | | | | 120 | | | | 125 | | | | | |
| tcc | cct | ccc | gtc | tcc | aat | ttc | ttc | acc | gtc | tct | ctc | gcc | gga | cct | cag | 491 |
| Ser | Pro | Pro | Val | Ser | Asn | Phe | Phe | Thr | Val | Ser | Leu | Ala | Gly | Pro | Gln | |
| | | 130 | | | | | 135 | | | | | 140 | | | | |
| ggg | aaa | gtc | atc | ggt | gga | ttc | gtc | gct | ggt | cct | ctc | gtt | gcc | gcc | gga | 539 |
| Gly | Lys | Val | Ile | Gly | Gly | Phe | Val | Ala | Gly | Pro | Leu | Val | Ala | Ala | Gly | |
| | 145 | | | | | 150 | | | | | 155 | | | | | |
| act | gtt | tac | ttc | gtc | gcc | act | agt | ttc | aag | aac | cct | tcc | tat | cac | cgg | 587 |
| Thr | Val | Tyr | Phe | Val | Ala | Thr | Ser | Phe | Lys | Asn | Pro | Ser | Tyr | His | Arg | |
| 160 | | | | | 165 | | | | | 170 | | | | | 175 | |
| tta | cct | gct | acg | gag | gaa | gag | caa | aga | aac | tcg | gcg | gaa | ggg | gaa | gag | 635 |
| Leu | Pro | Ala | Thr | Glu | Glu | Glu | Gln | Arg | Asn | Ser | Ala | Glu | Gly | Glu | Glu | |
| | | | | 180 | | | | | 185 | | | | | 190 | | |
| gag | gga | caa | tcg | ccg | ccg | gtc | tct | gga | ggt | ggt | gga | gag | tcg | atg | tac | 683 |
| Glu | Gly | Gln | Ser | Pro | Pro | Val | Ser | Gly | Gly | Gly | Gly | Glu | Ser | Met | Tyr | |
| | | | 195 | | | | | 200 | | | | | 205 | | | |
| gtg | ggt | ggc | tct | gat | gtc | att | tgg | gat | ccc | aac | gcc | aaa | gct | cca | tcg | 731 |
| Val | Gly | Gly | Ser | Asp | Val | Ile | Trp | Asp | Pro | Asn | Ala | Lys | Ala | Pro | Ser | |
| | | 210 | | | | | 215 | | | | | 220 | | | | |
| ccg | tac | tga | ccacaaatcc | | atctcgttca | | aactagggtt | | tcttcttctt | | | | | | | 780 |
| Pro | Tyr | | | | | | | | | | | | | | | |
| | 225 | | | | | | | | | | | | | | | |

| | | |
|---|---|---|
| tagatcatca agaatcaaca aaaagattgc attttagat tctttgtaat atcataattg | 840 |
| actcactctt taatctctct atacttctt ctttagcttt ttctgcagtg tcaaacttca | 900 |
| catatttgta gtttgatttg actatcccca agttttgtat tttatcatac aaattttgc | 960 |
| ctgtctctaa tggttgtttt ttcgtttgta taatcttatg cattgtttat tggagctcca | 1020 |
| gagattgaat gtataatata atggtttaat | 1050 |

<210> SEQ ID NO 8
<211> LENGTH: 225
<212> TYPE: PRT
<213> ORGANISM: Arabidopsis thaliana

<400> SEQUENCE: 8

Met Leu Ser Lys Leu Pro Thr Gln Arg His Leu His Leu Ser Pro Ser
1               5                   10                  15

Ser Pro Ser Met Glu Thr Val Gly Arg Pro Arg Gly Arg Pro Arg Gly
                20                  25                  30

Ser Lys Asn Lys Pro Lys Ala Pro Ile Phe Val Thr Ile Asp Pro Pro
            35                  40                  45

Met Ser Pro Tyr Ile Leu Glu Val Pro Ser Gly Asn Asp Val Val Glu
        50                  55                  60

Ala Leu Asn Arg Phe Cys Arg Gly Lys Ala Ile Gly Phe Cys Val Leu
65                  70                  75                  80

Ser Gly Ser Gly Ser Val Ala Asp Val Thr Leu Arg Gln Pro Ser Pro
                85                  90                  95

Ala Ala Pro Gly Ser Thr Ile Thr Phe His Gly Lys Phe Asp Leu Leu
            100                 105                 110

Ser Val Ser Ala Thr Phe Leu Pro Pro Leu Pro Pro Thr Ser Leu Ser
        115                 120                 125

Pro Pro Val Ser Asn Phe Phe Thr Val Ser Leu Ala Gly Pro Gln Gly
    130                 135                 140

Lys Val Ile Gly Gly Phe Val Ala Gly Pro Leu Val Ala Ala Gly Thr
145                 150                 155                 160

Val Tyr Phe Val Ala Thr Ser Phe Lys Asn Pro Ser Tyr His Arg Leu

-continued

```
                165                 170                 175
Pro Ala Thr Glu Glu Gln Arg Asn Ser Ala Glu Gly Glu Glu Glu
            180                 185                 190

Gly Gln Ser Pro Pro Val Ser Gly Gly Gly Glu Ser Met Tyr Val
        195                 200                 205

Gly Gly Ser Asp Val Ile Trp Asp Pro Asn Ala Lys Ala Pro Ser Pro
    210                 215                 220

Tyr
225
```

METHOD FOR MODIFYING PLANT BIOMASS

FIELD OF THE INVENTION

Figure 2:
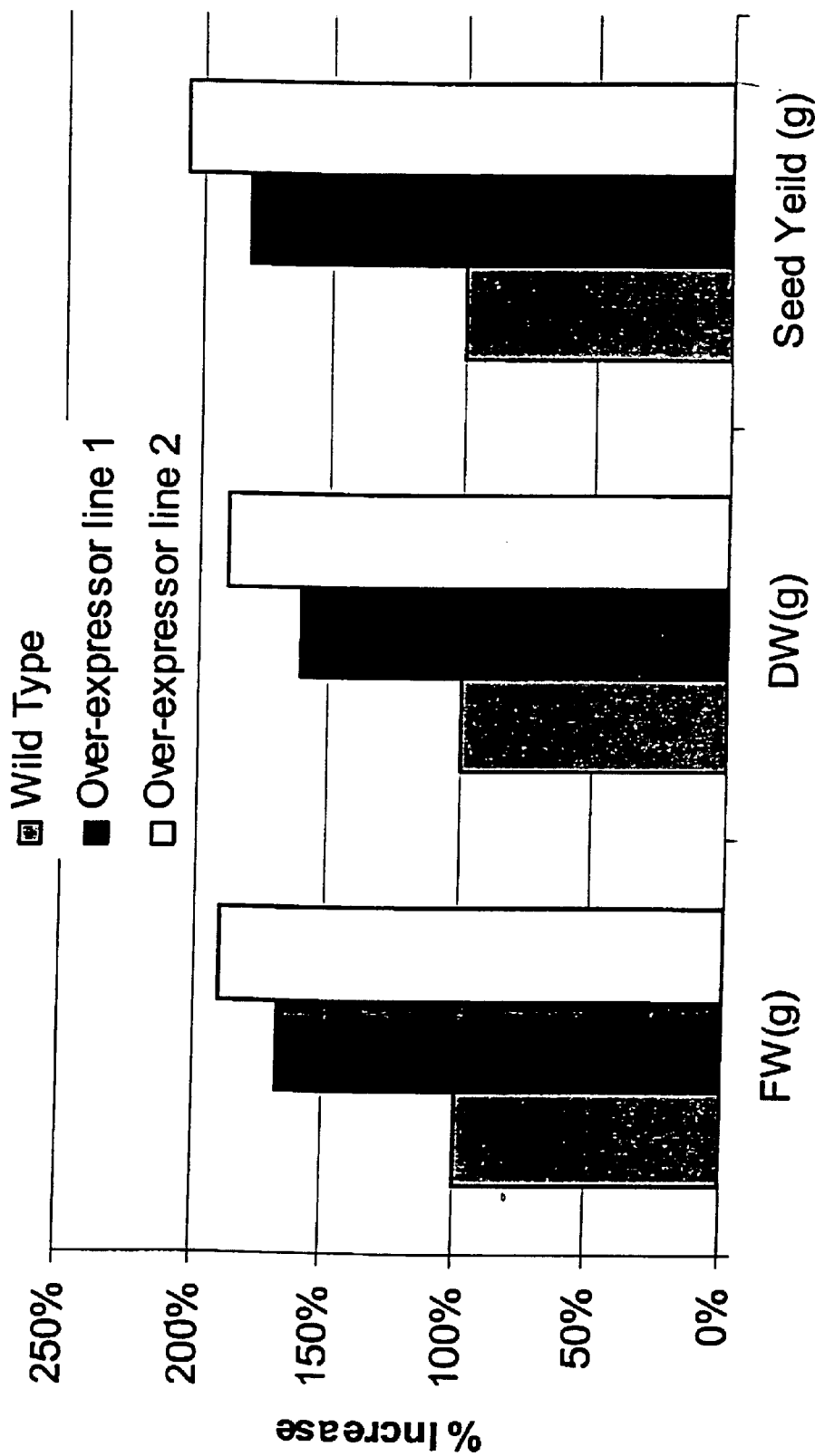

This invention relates to the field of plant biology. More particularly, the present invention pertains to compositions and methods for phenotypically modifying a plant.

BACKGROUND OF THE INVENTION

Increasing the biomass of a plant has several commercial applications. For example, increasing plant leaf biomass may increase the yield of leafy vegetables for human or animal consumption. Additionally, increasing leaf biomass can be used to increase production of plant-derived pharmaceutical or industrial products. By increasing plant biomass, increased production levels of the products may be obtained from the plants. Tobacco leaves, in particular, have been employed as plant factories to generate such products. Furthermore, it may be desirable to increase crop yields of plants by increasing total plant photosynthesis. An increase in total plant photosynthesis is typically achieved by increasing leaf area of the plant. Additional photosynthetic capacity may be used to increase the yield derived from particular plant tissue, including the leaves, roots, fruits or seed. In addition, the ability to modify the biomass of the leaves may be useful for permitting the growth of a plant under decreased light intensity or under high light intensity. Modification of the biomass of another tissue, such as roots, may be useful to improve a plant's ability to grow under harsh enviromental conditions, including drought or nutrient deprivation, because the roots may grow deeper into the ground.

Thus, the present invention provides a method for modifying the plant biomass by modifying the size or number of leaves or seed of a plant.

SUMMARY OF THE INVENTION

In a first aspect, the invention relates to a recombinant polynucleotide comprising a nucleotide sequence selected from the group consisting of: (a) a nucleotide sequence encoding a polypeptide comprising a sequence selected from SEQ ID Nos. 2N, where N=1–4, or a complementary nucleotide sequence thereof; (b) a nucleotide sequence encoding a polypeptide comprising a conservatively substituted variant of a polypeptide of (a); (c) a nucleotide sequence comprising a sequence selected from those of SEQ ID Nos. 2N–1, where N=1–4, or a complementary nucleotide sequence thereof; (d) a nucleotide sequence comprising silent substitutions in a nucleotide sequence of (c); (e) a nucleotide sequence which hybridizes under stringent conditions over substantially the entire length of a nucleotide sequence of one or more of: (a), (b), (c), or (d); (f) a nucleotide sequence comprising at least 15 consecutive nucleotides of a sequence of any of (a)–(e); (g) a nucleotide sequence comprising a subsequence or fragment of any of (a)–(f), which subsequence or fragment encodes a polypeptide having a biological activity that modifies a plant's biomass; (h) a nucleotide sequence having at least 40% sequence identity to a nucleotide sequence of any of (a)–(g); (i) a nucleotide sequence having at least 85% sequence identity to a nucleotide sequence of any of (a)–(g); (j) a nucleotide sequence which encodes a polypeptide having at least 40% sequence identity to a polypeptide of SEQ ID Nos. 2N, where N=1–4; (k) a nucleotide sequence which encodes a polypeptide having at least 85% identity sequence identity to a polypeptide of SEQ ID Nos. 2N, where N=1–4; and (1) a nucleotide sequence which encodes a conserved domain of a polypeptide having at least 65% sequence identity to a conserved domain of a polypeptide of SEQ ID Nos. 2N, where N=1–4. The recombinant polynucleotide may further comprise a constitutive, inducible, or tissue-active promoter operably linked to the nucleotide sequence. The invention also relates to compositions comprising at least two of the above described polynucleotides.

In a second aspect, the invention is an isolated or recombinant polypeptide comprising a subsequence of at least about 15 contiguous amino acids encoded by the recombinant or isolated polynucleotide described above. These polynucleotides and polypeptides are useful for modifying plant biomass, either by increasing or decreasing the size of the leaves, the roots, the flowers, the seeds, the stalk or the like.

In another aspect, the invention is a transgenic plant comprising one or more of the above described recombinant polynucleotides. In yet another aspect, the invention is a plant with altered expression levels of a polynucleotide described above or a plant with altered expression or activity levels of an above described polypeptide. In a further aspect, the invention relates to a cloning or expression vector comprising the isolated or recombinant polynucleotide described above or cells comprising the cloning or expression vector.

In yet a further aspect, the invention relates to a composition produced by incubating a polynucleotide of the invention with a nuclease, a restriction enzyme, a polymerase; a polymerase and a primer; a cloning vector, or with a cell.

Furthermore, the invention relates to a method for producing a plant having a modified plant biomass. The method comprises altering the expression of an isolated or recombinant polynucleotide of the invention or altering the expression or activity of a polypeptide of the invention in a plant to produce a modified plant, and selecting the modified plant for increased or decreased biomass.

In another aspect, the invention relates to a method of identifying a factor that is modulated by or interacts with a polypeptide encoded by a polynucleotide of the invention. The method comprises expressing a polypeptide encoded by the polynucleotide in a plant; and identifying at least one factor that is modulated by or interacts with the polypeptide. In one embodiment the method for identifying modulating or interacting factors is by detecting binding by the polypeptide to a promoter sequence, or by detecting interactions between an additional protein and the polypeptide in a yeast two hybrid system., or by detecting expression of a factor by hybridization to a microarray, subtractive hybridization or differential display.

In yet another aspect, the invention is a method of identifying a molecule that modulates activity or expression of a polynucleotide or polypeptide of interest. The method comprises placing the molecule in contact with a plant comprising the polynucleotide or polypeptide encoded by the polynucleotide of the invention and monitoring one or more of the expression level of the polynucleotide in the plant, the expression level of the polypeptide in the plant, and modulation of an activity of the polypeptide in the plant.

In yet another aspect, the invention relates to an integrated system, computer or computer readable medium comprising one or more character strings corresponding to a polynucleotide of the invention, or to a polypeptide encoded by the polynucleotide. The integrated system, computer or computer readable medium may comprise a link between one or more sequence strings to a modified biomass phenotype.

In yet another aspect, the invention is a method for identifying a sequence similar or homologous to one or more polynucleotides of the invention, or one or more polypeptides encoded by the polynucleotides. The method comprises providing a sequence database; and, querying the sequence database with one or more target sequences corresponding to the one or more polynucleotides or to the one or more polypeptides to identify one or more sequence members of the database that display sequence similarity or homology to one or more of the one or more target sequences.

BRIEF DESCRIPTION OF THE SEQUENCE LISTING AND DRAWINGS

The Sequence Listing provides exemplary polynucleotide and polypeptide sequences of the invention. These sequences may be employed to modify the biomass of a plant.

Figure 1:
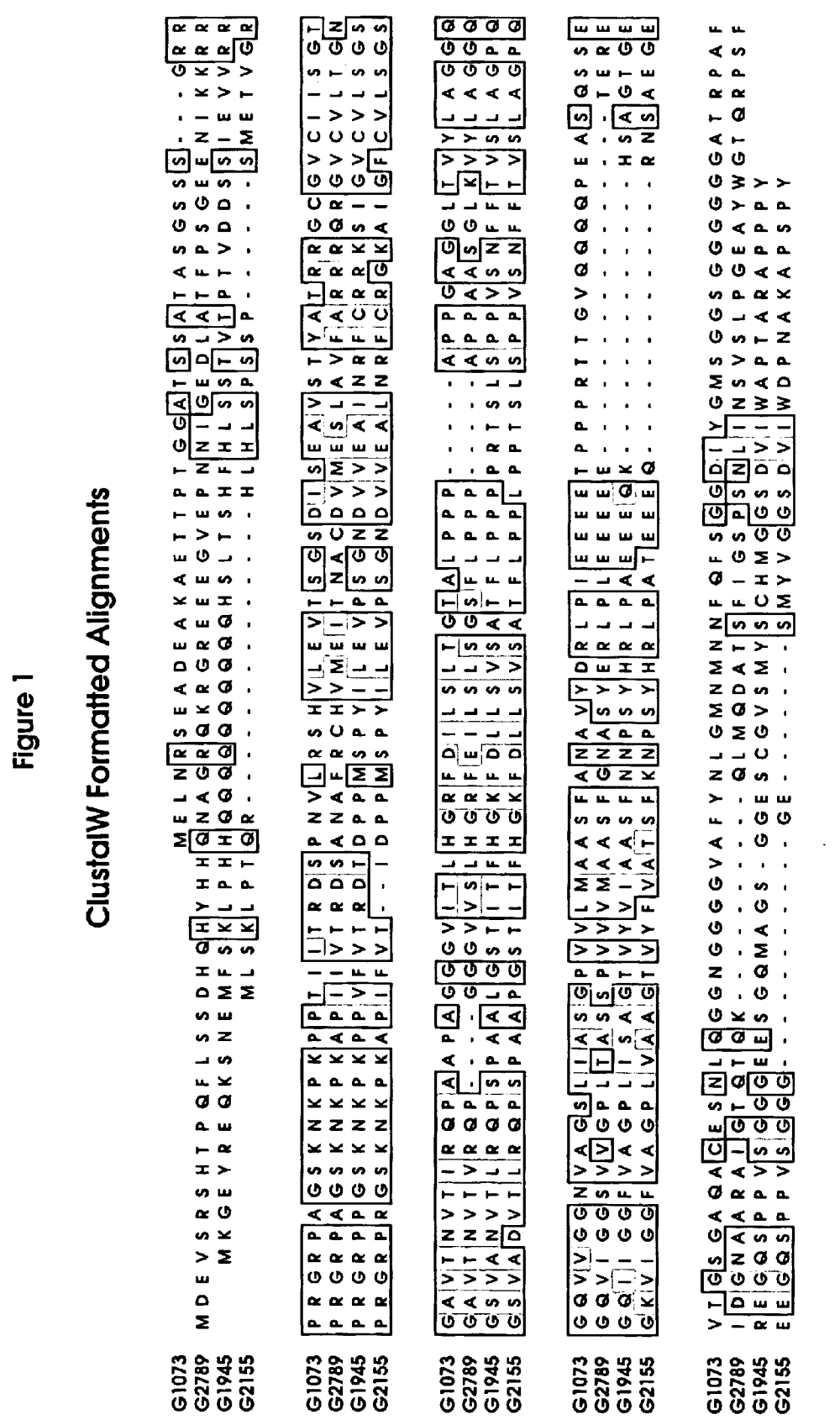

FIG. 1 shows the polypeptide alignments for G1073 (SEQ ID Nos. 1 and 2), G2789 (SEQ ID Nos. 3 and 4), G1945 (SEQ ID Nos. 5 and 6) and G2155 (SEQ ID Nos. 7 and 8) showing regions of the polypeptides with sequence identity.

FIG. 2 shows that plants overexpressing G1073 have an increased fresh weight, dry weight and seed yield (greater than 150%) when compared with plants that do not overexpress G1073.

DETAILED DESCRIPTION

The present invention relates to polynucleotides and polypeptides, e.g. for modifying phenotypes of plants.

In particular, the polynucleotides or polypeptides are useful for modifying plant biomass when the expression levels of the polynucleotides or expression levels or activity levels of the polypeptides are altered compared with those found in a wild type plant. Plant biomass can be either decreased, increased or made inducible under specific conditions using the polynucleotides or polypeptides of this invention.

The polynucleotides of the invention encode plant transcription factors. The plant transcription factors are derived, e.g., from *Arabidopsis thaliana* and can belong, e.g., to one or more of the following transcription factor families: the AP2 (APETALA2) domain transcription factor family (Riechmann and Meyerowitz (1998) *J. Biol. Chem.* 379:633–646); the MYB transcription factor family (Martin and Paz-Ares (1997) *Trends Genet.* 13:67–73); the MADS domain transcription factor family (Riechmann and Meyerowitz (1997) *J. Biol. Chem* 378:1079–1101); the WRKY protein family (Ishiguro and Nakamura (1994) *Mol. Gen. Genet.* 244:563–571); the ankyrin-repeat protein family (Zhang et al. (1992) *Plant Cell* 4:1575–1588); the miscellaneous protein (MISC) family (Kim et al. (1997) *Plant J.* 11:1237–1251); the zinc finger protein (Z) family (Klug and Schwabe (1995) *FASEB J.* 9:597–604); the homeobox (HB) protein family (Duboule (1994) *Guidebook to the Homeobox Genes,* Oxford University Press); the CAAT-element binding proteins (Forsburg and Guarente (1989) *Genes Dev.* 3:1166–1178); the squamosa promoter binding proteins (SPB) (Klein et al. (1996) *Mol. Gen. Genet.* 1996 250:7–16); the NAM protein family; the IAA/AUX proteins (Rouse et al. (1998) *Science* 279:1371–1373); the HLH/MYC protein family (Littlewood et al. (1994) *Prot. Profile* 1:639–709); the DNA-binding protein (DBP) family (Tucker et al. (1994) *EMBO J.* 13:2994–3002); the bZIP family of transcription factors (Foster et al. (1994) *FASEB J.* 8:192–200); the BPF-1 protein (Box P-binding factor) family (da Costa e Silva et al. (1993) *Plant J.* 4:125–135); the golden protein (GLD) family (Hall et al. (1998) *Plant Cell* 10:925–936); and the AT-hook protein (AT-Hook) family (Aravind et al. (1998) *Nucl. Acid Res.* 26: 4413–4421). Exemplary transcription factors of the present invention are listed in the Sequence Listing.

In addition to methods for modifying a plant phenotype by employing one or more polynucleotides and polypeptides of the invention described herein, the polynucleotides and polypeptides of the invention have a variety of additional uses. These uses include their use in the recombinant production (i.e, expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like, of as substrates for cloning e.g., including digestion or ligation reactions, and for identifying exogenous or endogenous modulators of the transcription factors.

Definitions

A "polynucleotide" is a nucleic acid sequence comprising a plurality of polymerized nucleotide residues, e.g., at least about 15 consecutive polymerized nucleotide residues, optionally at least about 30 consecutive nucleotides, at least about 50 consecutive nucleotides. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single stranded or double stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

A "recombinant polypeptide" is a polypeptide produced by translation of a recombinant polynucleotide. An "isolated polypeptide," whether a naturally occurring or a recombinant polypeptide, is more enriched in (or out of) a cell than the polypeptide in its natural state in a wild type cell, e.g., more than about 5% enriched, more than about 10% enriched, or more than about 20%, or more than about 50%, or more, enriched, i.e., alternatively denoted: 105%, 110%, 120%, 150%, 300% or more, enriched relative to wild type standardized at 100%. Such an enrichment is not the result of a natural response of a wild type plant. Alternatively, or additionally, the isolated polypeptide is separated from other cellular components with which it is typically associated, e.g., by any of the various protein purification methods herein.

The term "transgenic plant" refers to a plant that contains genetic material, not found in a wild type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation.

A transgenic plant may contain an expression vector or cassette. The expression cassette typically comprises a polypeptide-encoding sequence operably linked (i.e., under regulatory control of) to appropriate inducible or constitutive regulatory sequences that allow for the expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

The phrase "ectopically expression or altered expression" in reference to a polynucleotide indicates that the pattern of expression in, e.g., a transgenic plant or plant tissue, is different from the expression pattern in a wild type plant or a reference plant of the same species. For example, the polynucleotide or polypeptide is expressed in a cell or tissue type other than a cell or tissue type in which the sequence is expressed in the wild type plant, or by expression at a time other than at the time the sequence is expressed in the wild type plant, or by a response to different inducible agents, such as hormones or environmental signals, or at different expression levels (either higher or lower) compared with those found in a wild type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "fragment" or "domain," with respect to a polypeptide, refers to a subsequence of the polypeptide. In some cases, the fragment or domain, is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA binding domain that binds to a DNA promoter region, an activation domain or a domain for protein-protein interactions. Fragments can vary in size from as few as 6 amino acids to the full length of the intact polypeptide, but are preferably at least about 30 amino acids in length and more preferably at least about 60 amino acids in length. In reference to a nucleotide sequence, "a fragment" refers to any subsequence of a polynucleotide, typically, of at least consecutive about 15 nucleotides, preferably at least about 30 nucleotides, more preferably at least about 50, of any of the sequences provided herein.

The term "trait" refers to a physiological, morphological, biochemical or physical characteristic of a plant or particular plant material or cell. In some instances, this characteristic is visible to the human eye, such as seed or plant size, or can be measured by available biochemical techniques, such as the protein, starch or oil content of seed or leaves or by the observation of the expression level of genes, e.g., by employing Northern analysis, RT-PCR, microarray gene expression assays or reporter gene expression systems, or by agricultural observations such as stress tolerance, yield or pathogen tolerance.

"Trait modification" refers to a detectable difference in a characteristic in a plant ectopically expressing a polynucleotide or polypeptide of the present invention relative to a plant not doing so, such as a wild type plant. In some cases, the trait modification can be evaluated quantitatively. For example, the trait modification can entail at least about a 2% increase or decrease in an observed trait (difference), at least a 5% difference, at least about a 10% difference, at least about a 20% difference, at least about a 30%, at least about a 50%, at least about a 70%, or at least about a 100%, at least a 300% or an even greater difference. It is known that there can be a natural variation in the modified trait. Therefore, the trait modification observed entails a change of the normal distribution of the trait in the plants compared with the distribution observed in wild type plant.

Polypeptides and Polynucleotides of the Invention

The present invention provides, among other things, transcription factors (TFs), and transcription factor homologue polypeptides, and isolated or recombinant polynucleotides encoding the polypeptides. These polypeptides and polynucleotides may be employed to modify a plant's biomass.

Exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known transcription factors. Polynucleotide sequences meeting such criteria were confirmed as transcription factors.

Additional polynucleotides of the invention were identified by screening *Arabidopsis thaliana* and/or other plant cDNA libraries with probes corresponding to known transcription factors under low stringency hybridization conditions. Additional sequences, including full length coding sequences were subsequently recovered by the rapid amplification of cDNA ends (RACE) procedure, using a commercially available kit according to the manufacturer's instructions. Where necessary, multiple rounds of RACE are performed to isolate 5' and 3' ends. The full length cDNA was then recovered by a routine end-to-end polymerase chain reaction (PCR) using primers specific to the isolated 5' and 3' ends. Exemplary sequences are provided in the Sequence Listing.

The polynucleotides of the invention were ectopically expressed in overexpressor or knockout plants and changes in plant biomass was observed. Therefore, the polynucleotides and polypeptides can be employed to improve (increase or decrease) plant biomass.

Making Polynucleotides

The polynucleotides of the invention include sequences that encode transcription factors and transcription factor homologue polypeptides and sequences complementary thereto, as well as unique fragments of coding sequence, or sequence complementary thereto. Such polynucleotides can be, e.g., DNA or RNA, e.g., mRNA, cRNA, synthetic RNA, genomic DNA, cDNA synthetic DNA, oligonucleotides, etc. The polynucleotides are either double-stranded or single-stranded, and include either, or both sense (i.e., coding) sequences and antisense (i.e., non-coding, complementary) sequences. The polynucleotides include the coding sequence of a transcription factor, or transcription factor homologue polypeptide, in isolation, in combination with additional coding sequences (e.g., a purification tag, a localization signal, as a fusion-protein, as a pre-protein, or the like), in combination with non-coding sequences (e.g., introns or inteins, regulatory elements such as promoters, enhancers, terminators, and the like), and/or in a vector or host environment in which the polynucleotide encoding a transcription factor or transcription factor homologue polypeptide is an endogenous or exogenous gene.

A variety of methods exist for producing the polynucleotides of the invention. Procedures for identifying and isolating DNA clones are well known to those of skill in the art, and are described in, e.g., Berger and Kinmmel, *Guide to Molecular Cloning Techniques, Methods in Enzymology* volume 152 Academic Press, Inc., San Diego, Calif. ("Berger"); Sambrook et al., *Molecular Cloning—A Laboratory Manual* (2nd Ed.), Vol. 1–3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2000) ("Ausubel").

Alternatively, polynucleotides of the invention, can be produced by a variety of in vitro amplification methods adapted to the present invention by appropriate selection of specific or degenerate primers. Examples of protocols sufficient to direct persons of skill through in vitro amplification methods, including the polymerase chain reaction (PCR) the ligase chain reaction (LCR), Qbeta-replicase amplification and other RNA polymerase mediated techniques (e.g., NASBA), e.g., for the production of the homologous nucleic acids of the invention are found in Berger, Sambrook, and Ausubel, as well as Mullis et al., (1987) *PCR Protocols A Guide to Methods and Applications* (Innis et al. eds) Academic Press Inc. San Diego, Calif. (1990) (Innis). Improved methods for cloning in vitro amplified nucleic acids are described in Wallace et al., U.S. Pat. No. 5,426,039. Improved methods for amplifying large nucleic acids by PCR are summarized in Cheng et al. (1994) *Nature* 369: 684–685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

Alternatively, polynucleotides and oligonucleotides of the invention can be assembled from fragments produced by solid-phase synthesis methods. Typically, fragments of up to approximately 100 bases are individually synthesized and then enzymatically or chemically ligated to produce a desired sequence, e.g., a polynucletotide encoding all or part of a transcription factor. For example, chemical synthesis using the phosphoramidite method is described, e.g., by Beaucage et al. (1981) *Tetrahedron Letters* 22:1859–69; and Matthes et al. (1984) *EMBO J*. 3:801–5. According to such methods, oligonucleotides are synthesized, purified, annealed to their complementary strand, ligated and then optionally cloned into suitable vectors. And if so desired, the polynucleotides and polypeptides of the invention can be custom ordered from any of a number of commercial suppliers.

Homologous Sequences

Sequences homologous, i.e., that share significant sequence identity or similarity, to those provided in the Sequence Listing, derived from *Arabidopsis thaliana* or from other plants of choice are also an aspect of the invention. Homologous sequences can be derived from any plant including monocots and dicots and in particular agriculturally important plant species, including but not limited to, crops such as soybean, wheat, corn, potato, cotton, rice, oilseed rape (including canola), sunflower, alfalfa, sugarcane and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, spinach, squash, sweet corn, tobacco, tomato, watermelon, rosaceous fruits (such as apple, peach, pear, cherry and plum) and vegetable brassicas (such as broccoli, cabbage, cauliflower, brussel sprouts and kohlrabi). Other crops, fruits and vegetables whose phenotype can be changed include barley, rye, millet, sorghum, currant, avocado, citrus fruits such as oranges, lemons, grapefruit and tangerines, artichoke, cherries, nuts such as the walnut and peanut, endive, leek, roots, such as arrowroot, beet, cassava, turnip, radish, yam, and sweet potato, and beans. The homologous sequences may also be derived from woody species, such pine, poplar and eucalyptus.

Transcription factors that are homologous to the listed sequences will typically share at least about 35% amino acid sequence identity. More closely related transcription factors can share at least about 50%, about 60%, about 65%, about 70%, about 75% or about 80% or about 90% or about 95% or about 98% or more sequence identity with the listed sequences. Factors that are most closely related to the listed sequences share, e.g., at least about 85%, about 90% or about 95% or more % sequence identity to the listed sequences. At the nucleotide level, the sequences will typically share at least about 40% nucleotide sequence identity, preferably at least about 50%, about 60%, about 70% or about 80% sequence identity, and more preferably about 85%, about 90%, about 95% or about 97% or more sequence identity to one or more of the listed sequences. The degeneracy of the genetic code enables major variations in the nucleotide sequence of a polynucleotide while maintaining the amino acid sequence of the encoded protein. Conserved domains within a transcription factor family may exhibit a higher degree of sequence homology, such as at least 65% sequence identity including conservative substitutions, and preferably at least 80% sequence identity. Exemplary conserved domains of the present invention include for example, for G1073 (SEQ ID Nos. 1 and 2) amino acid residues 35 through 40 or 42 through 48 which are conserved in each of the sequences G2789 (SEQ ID Nos. 3 and 4), G1945 (SEQ ID Nos. 5 and 6) and G2155 (SEQ ID Nos. 7 and 8).

Identifying Nucleic Acids by Hybridization

Polynucleotides homologous to the sequences illustrated in the Sequence Listing can be identified, e.g., by hybridization to each other under stringent or under highly stringent conditions. Single stranded polynucleotides hybridize when they associate based on a variety of well characterized physico-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number), as described in more detail in the references cited above.

An example of stringent hybridization conditions for hybridization of complementary nucleic acids which have more than 100 complementary residues on a filter in a Southern or northern blot is about 5° C. to 20° C. lower than the thermal melting point (Tm) for the specific sequence at a defined ionic strength and pH. The $T_m$ is the temperature (under defined ionic strength and pH) at which 50% of the target sequence hybridizes to a perfectly matched probe. Nucleic acid molecules that hybridize under stringent conditions will typically hybridize to a probe based on either the entire cDNA or selected portions, e.g., to a unique subsequence, of the cDNA under wash conditions of 0.2× SSC to 2.0× SSC, 0.1% SDS at 50–65° C., for example 0.2× SSC, 0.1% SDS at 65° C. For identification of less closely related homologues washes can be performed at a lower temperature, e.g., 50° C. In general, stringency is increased by raising the wash temperature and/or decreasing the concentration of SSC.

As another example, stringent conditions can be selected such that an oligonucleotide that is perfectly complementary to the coding oligonucleotide hybridizes to the coding oligonucleotide with at least about a 5–10× higher signal to noise ratio than the ratio for hybridization of the perfectly complementary oligonucleotide to a nucleic acid encoding a transcription factor known as of the filing date of the application. Conditions can be selected such that a higher signal to noise ratio is observed in the particular assay which is used, e.g., about 15×, 25×, 35×, 50× or more. Accordingly, the subject nucleic acid hybridizes to the unique coding oligonucleotide with at least a 2× higher signal to noise ratio as compared to hybridization of the coding oligonucleotide to a nucleic acid encoding known polypeptide. Again, higher signal to noise ratios can be selected, e.g., about 5×, 10×, 25×, 35×, 50× or more. The particular signal will depend on the label used in the relevant assay, e.g., a fluorescent label, a colorimetric label, a radioactive label, or the like.

Alternatively, transcription factor homologue polypeptides can be obtained by screening an expression library using antibodies specific for one or more transcription factors. With the provision herein of the disclosed transcription factor, and transcription factor homologue nucleic acid sequences, the encoded polypeptide(s) can be expressed and purified in a heterologous expression system (e.g., *E. coli*) and used to raise antibodies (monoclonal or polyclonal) specific for the polypeptide(s) in question. Antibodies can also be raised against synthetic peptides derived from transcription factor, or transcription factor homologue, amino acid sequences. Methods of raising antibodies are well known in the art and are described in Harlow and Lane (1988) *Antibodies: A Laboratory Manual*, Cold Spring Harbor Laboratory, N.Y. Such antibodies can then be used to screen an expression library produced from the plant from which it is desired to clone additional transcription factor homologues, using the methods described above. The selected cDNAs can be confirmed by sequencing and enzymatic activity.

Sequence Variations

It will readily be appreciated by those of skill in the art, that any of a variety of polynucleotide sequences are capable of encoding the transcription factors and transcription factor homologue polypeptides of the invention. Due to the degeneracy of the genetic code, many different polynucleotides can encode identical and/or substantially similar polypeptides in addition to those sequences illustrated in the Sequence Listing.

For example, Table 1 illustrates, e.g., that the codons AGC, AGT, TCA, TCC, TCG, and TCT all encode the same amino acid:serine. Accordingly, at each position in the sequence where there is a codon encoding serine, any of the above trinucleotide sequences can be used without altering the encoded polypeptide.

TABLE 1

| Amino acids | | | Codon | | | | |
|---|---|---|---|---|---|---|---|
| Alanine | Ala | A | GCA | GCC | GCG | GCU | |
| Cysteine | Cys | C | TGC | TGT | | | |
| Aspartic acid | Asp | D | GAC | GAT | | | |
| Glutamic acid | Glu | E | GAA | GAG | | | |
| Phenylalanine | Phe | F | TTC | TTT | | | |
| Glycine | Gly | G | GGA | GGC | GGG | GGT | |
| Histidine | His | H | CAC | CAT | | | |
| Isoleucine | Ile | I | ATA | ATC | ATT | | |
| Lysine | Lys | K | AAA | AAG | | | |
| Leucine | Leu | L | TTA | TTG | CTA | CTC | CTG | CTT |
| Methionine | Met | M | ATG | | | | |
| Asparagine | Asn | N | AAC | AAT | | | |
| Proline | Pro | P | CCA | CCC | CCG | CCT | |
| Glutamine | Gln | Q | CAA | CAG | | | |
| Arginine | Arg | R | AGA | AGG | CGA | CGC | CGG | CGT |
| Serine | Ser | S | AGC | AGT | TCA | TCC | TCG | TCT |
| Threonine | Thr | T | ACA | ACC | ACG | ACT | |
| Valine | Val | V | GTA | GTC | GTG | GTT | |
| Tryptophan | Trp | W | TGG | | | | |
| Tyrosine | Tyr | Y | TAC | TAT | | | |

Sequence alterations that do not change the amino acid sequence encoded by the polynucleotide are termed "silent" variations. With the exception of the codons ATG and TGG, encoding methionine and tryptophan, respectively, any of the possible codons for the same amino acid can be substituted by a variety of techniques, e.g., site-directed mutagenesis, available in the art. Accordingly, any and all such variations of a sequence selected from the above table are a feature of the invention.

In addition to silent variations, other conservative variations that alter one, or a few amino acids in the encoded polypeptide, can be made without altering the function of the polypeptide, these conservative variants are, likewise, a feature of the invention.

For example, substitutions, deletions and insertions introduced into the sequences provided in the Sequence Listing are also envisioned by the invention. Such sequence modifications can be engineered into a sequence by site-directed mutagenesis (Wu (ed.) *Meth. Enzymol.* (1993) vol. 217, Academic Press) or the other methods noted below. Amino acid substitutions are typically of single residues; insertions usually will be on the order of about from 1 to 10 amino acid residues; and deletions will range about from 1 to 30 residues. In preferred embodiments, deletions or insertions are made in adjacent pairs, e.g., a deletion of two residues or insertion of two residues. Substitutions, deletions, insertions or any combination thereof can be combined to arrive at a sequence. The mutations that are made in the polynucleotide encoding the transcription factor should not place the sequence out of reading frame and should not create complementary regions that could produce secondary mRNA structure. Preferably, the polypeptide encoded by the DNA performs the desired function.

Conservative substitutions are those in which at least one residue in the amino acid sequence has been removed and a different residue inserted in its place. Such substitutions generally are made in accordance with the Table 2 when it is desired to maintain the activity of the protein. Table 2 shows amino acids which can be substituted for an amino acid in a protein and which are typically regarded as conservative substitutions.

TABLE 2

| Residue | Conservative Substitutions |
| --- | --- |
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Substitutions that are less conservative than those in Table 2 can be selected by picking residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Further Modifying Sequences of the Invention—Mutation/Forced Evolution

In addition to generating silent or conservative substitutions as noted, above, the present invention optionally includes methods of modifying the sequences of the Sequence Listing. In the methods, nucleic acid or protein modification methods are used to alter the given sequences to produce new sequences and/or to chemically or enzymatically modify given sequences to change the properties of the nucleic acids or proteins.

Thus, in one embodiment, given nucleic acid sequences are modified, e.g., according to standard mutagenesis or artificial evolution methods to produce modified sequences. For example, Ausubel, supra, provides additional details on mutagenesis methods. Artificial forced evolution methods are described, e.g., by Stemmer (1994) *Nature* 370:389–391, and Stemmer (1994) *Proc. Natl. Acad. Sci. USA* 91:10747–10751. Many other mutation and evolution methods are also available and expected to be within the skill of the practitioner.

Similarly, chemical or enzymatic alteration of expressed nucleic acids and polypeptides can be performed by standard methods. For example, sequence can be modified by addition of lipids, sugars, peptides, organic or inorganic compounds, by the inclusion of modified nucleotides or amino acids, or the like. For example, protein modification techniques are illustrated in Ausubel, supra. Further details on chemical and enzymatic modifications can be found herein. These modification methods can be used to modify any given sequence, or to modify any sequence produced by the various mutation and artificial evolution modification methods noted herein.

Accordingly, the invention provides for modification of any given nucleic acid by mutation, evolution, chemical or enzymatic modification, or other available methods, as well as for the products produced by practicing such methods, e.g., using the sequences herein as a starting substrate for the various modification approaches.

For example, optimized coding sequence containing codons preferred by a particular prokaryotic or eukaryotic host can be used e.g., to increase the rate of translation or to produce recombinant RNA transcripts having desirable properties, such as a longer half-life, as compared with transcripts produced using a non-optimized sequence. Translation stop codons can also be modified to reflect host preference. For example, preferred stop codons for *S. cerevisiae* and mammals are TAA and TGA, respectively. The preferred stop codon for monocotyledonous plants is TGA, whereas insects and *E. coli* prefer to use TAA as the stop codon.

The polynucleotide sequences of the present invention can also be engineered in order to alter a coding sequence for a variety of reasons, including but not limited to, alterations which modify the sequence to facilitate cloning, processing and/or expression of the gene product. For example, alterations are optionally introduced using techniques which are well known in the art, e.g., site-directed mutagenesis, to insert new restriction sites, to alter glycosylation patterns, to change codon preference, to introduce splice sites, etc.

Furthermore, a fragment or domain derived from any of the polypeptides of the invention can be combined with domains derived from other transcription factors or synthetic domains to modify the biological activity of a transcription factor. For instance, a DNA binding domain derived from a transcription factor of the invention can be combined with the activation domain of another transcription factor or with a synthetic activation domain. A transcription activation domain assists in initiating transcription from a DNA binding site. Examples include the transcription activation region of VP16 or GAL4 (Moore et al. (1998) *Proc. Natl. Acad. Sci. USA* 95: 376–381; and Aoyama et al. (1995) *Plant Cell* 7:1773–1785), peptides derived from bacterial sequences (Ma and Ptashne (1987) *Cell* 51; 113–119) and synthetic peptides (Giniger and Ptashne, (1987) *Nature* 330:670–672).

Expression and Modification of Polypeptides

Typically, polynucleotide sequences of the invention are incorporated into recombinant DNA (or RNA) molecules that direct expression of polypeptides of the invention in appropriate host cells, transgenic plants, in vitro translation systems, or the like. Due to the inherent degeneracy of the genetic code, nucleic acid sequences which encode substantially the same or a functionally equivalent amino acid sequence can be substituted for any listed sequence to provide for cloning and expressing the relevant homologue.

Vectors, Promoters and Expression Systems

The present invention includes recombinant constructs comprising one or more of the nucleic acid sequences herein. The constructs typically comprise a vector, such as a plasmid, a cosmid, a phage, a virus (e.g., a plant virus), a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts which describe molecular biological techniques useful herein, including the use and production of vectors, promoters and many other relevant topics, include Berger, Sambrook and Ausubel, supra. Any of the identified sequences can be incorporated into a cassette or vector, e.g., for expression in plants. A number of expression vectors suitable for stable transformation of plant cells or for the establishment of transgenic plants have been described including those described in Weissbach and Weissbach, (1989) *Methods for Plant Molecular Biology*, Academic Press, and Gelvin et al., (1990) *Plant Molecular Biology Manual*, Kluwer Academic Publishers. Specific examples include those derived from a Ti plasmid of *Agrobacterium tumefaciens*, as well as those disclosed by Herrera-Estrella et al. (1983) *Nature* 303: 209, Bevan (1984) *Nucl Acid Res.* 12: 8711–8721, Klee (1985) *Bio/Technology* 3: 637–642, for dicotyledonous plants.

Alternatively, non-Ti vectors can be used to transfer the DNA into monocotyledonous plants and cells by using free DNA delivery techniques. Such methods can involve, for example, the use of liposomes, electroporation, microprojectile bombardment, silicon carbide whiskers, and viruses. By using these methods transgenic plants such as wheat, rice (Christou (1991) *Bio/Technology* 9: 957–962) and corn (Gordon-Kamm (1990) *Plant Cell* 2: 603–618) can be produced. An immature embryo can also be a good target tissue for monocots for direct DNA delivery techniques by using the particle gun (Weeks et al. (1993) *Plant Physiol* 102: 1077–1084; Vasil (1993) *Bio/Technology* 10: 667–674; Wan and Lemeaux (1994) *Plant Physiol* 104: 37–48, and for Agrobacterium-mediated DNA transfer (Ishida et al. (1996) *Nature Biotech* 14: 745–750).

Typically, plant transformation vectors include one or more cloned plant coding sequence (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally-or developmentally-regulated, or cell- or tissue-specific expression), a transcription initiation start site, an RNA processing signal (such as intron splice sites), a transcription termination site, and/or a polyadenylation signal.

Examples of constitutive plant promoters which can be useful for expressing the TF sequence include: the cauliflower mosaic virus (CaMV) 35S promoter, which confers constitutive, high-level expression in most plant tissues (see, e.g., Odel et al. (1985) *Nature* 313:810); the nopaline synthase promoter (An et al. (1988) *Plant Physiol* 88:547); and the octopine synthase promoter (Fromm et al. (1989) *Plant Cell* 1: 977).

A variety of plant gene promoters that regulate gene expression in response to environmental, hormonal, chemical, developmental signals, and in a tissue-active manner can be used for expression of a TF sequence in plants. Choice of a promoter is based largely on the phenotype of interest and is determined by such factors as tissue (e.g., seed, fruit, root, pollen, vascular tissue, flower, carpel, etc.), inducibility (e.g., in response to wounding, heat, cold, drought, light, pathogens, etc.), timing, developmental stage, and the like. Numerous known promoters have been characterized and can favorable be employed to promote expression of a polynucleotide of the invention in a transgenic plant or cell of interest. For example, tissue specific promoters include: seed-specific promoters (such as the napin, phaseolin or DC3 promoter described in U.S. Pat. No. 5,773,697), fruit-specific promoters that are active during fruit ripening (such as the dru 1 promoter (U.S. Pat. No. 5,783,393), or the 2A11 promoter (U.S. Pat. No. 4,943,674) and the tomato polygalacturonase promoter (Bird et al. (1988) *Plant Mol Biol* 11:651), root-specific promoters, such as those disclosed in U.S. Pat. Nos. 5,618,988, 5,837,848 and 5,905,186, pollen-active promoters such as PTA29, PTA26 and PTA13 (U.S. Pat. No. 5,792,929), promoters active in vascular tissue (Ringli and Keller (1998) *Plant Mol Biol* 37:977–988), flower-specific (Kaiser et al, (1995) *Plant Mol Biol* 28:231–243), pollen (Baerson et al. (1994) *Plant Mol Biol* 26:1947–1959), carpels (Ohl et al. (1990) *Plant Cell* 2:837–848), pollen and ovules (Baerson et al. (1993) *Plant Mol Biol* 22:255–267), auxin-inducible promoters (such as that described in van der Kop et al. (1999) *Plant Mol Biol* 39:979–990 or Baumann et al. (1999) *Plant Cell* 11:323–334), cytokinin-inducible promoter (Guevara-Garcia (1998) *Plant Mol Biol* 38:743–753), promoters responsive to gibberellin (Shi et al. (1998) *Plant Mol Biol* 38:1053–1060, Willmott et al. (1998) 38:817–825) and the like. Additional promoters are those that elicit expression in response to heat (Ainley et al. (1993) *Plant Mol Biol* 22: 13–23), light (e.g., the pea rbcS-3A promoter, Kuhlemeier et al. (1989) *Plant Cell* 1:471, and the maize rbcS promoter, Schaffner and Sheen (1991) *Plant Cell* 3: 997); wounding (e.g., wunl, Siebertz et al. (1989) *Plant Cell* 1: 961); pathogens (such as the PR-1 promoter described in Buchel et al. (1999) *Plant Mol. Biol.* 40:387–396, and the PDF1.2 promoter described in Manners et al. (1998) *Plant Mol. Biol.* 38:1071–80), and chemicals such as methyl jasmonate or salicylic acid (Gatz et al. (1997) *Plant Mol Biol* 48: 89–108). In addition, the timing of the expression can be controlled by using promoters such as those acting at senescence (An and Amazon (1995) *Science* 270: 1986–1988); or late seed development (Odell et al. (1994) *Plant Physiol* 106:447–458).

Plant expression vectors can also include RNA processing signals that can be positioned within, upstream or downstream of the coding sequence. In addition, the expression vectors can include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Additional Expression Elements

Specific initiation signals can aid in efficient translation of coding sequences. These signals can include, e.g., the ATG initiation codon and adjacent sequences. In cases where a coding sequence, its initiation codon and upstream sequences are inserted into the appropriate expression vector, no additional translational control signals may be needed. However, in cases where only coding sequence (e.g., a mature protein coding sequence), or a portion thereof, is inserted, exogenous transcriptional control signals including the ATG initiation codon can be separately provided. The initiation codon is provided in the correct reading frame to facilitate transcription. Exogenous transcriptional elements and initiation codons can be of various origins, both natural and synthetic. The efficiency of expression can be enhanced by the inclusion of enhancers appropriate to the cell system in use.

Expression Hosts

The present invention also relates to host cells which are transduced with vectors of the invention, and the production of polypeptides of the invention (including fragments thereof) by recombinant techniques. Host cells are genetically engineered (i.e, nucleic acids are introduced, e.g., transduced, transformed or transfected) with the vectors of this invention, which may be, for example, a cloning vector or an expression vector comprising the relevant nucleic acids herein. The vector is optionally a plasmid, a viral particle, a phage, a naked nucleic acids, etc. The engineered host cells can be cultured in conventional nutrient media modified as appropriate for activating promoters, selecting transformants, or amplifying the relevant gene. The culture conditions, such as temperature, pH and the like, are those previously used with the host cell selected for expression, and will be apparent to those skilled in the art and in the references cited herein, including, Sambrook and Ausubel.

The host cell can be a eukaryotic cell, such as a yeast cell, or a plant cell, or the host cell can be a prokaryotic cell, such as a bacterial cell. Plant protoplasts are also suitable for some applications. For example, the DNA fragments are introduced into plant tissues, cultured plant cells or plant protoplasts by standard methods including electroporation (Fromm et al., (1985) *Proc. Natl. Acad. Sci. USA* 82, 5824, infection by viral vectors such as cauliflower mosaic virus (CaMV) (Hohn et al., (1982) *Molecular Biology of Plant Tumors,* (Academic Press, New York) pp. 549–560; U.S. Pat. No. 4,407,956), high velocity ballistic penetration by small particles with the nucleic acid either within the matrix of small beads or particles, or on the surface (Klein et al., (1987) *Nature* 327, 70–73), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233:496–498; Fraley et al. (1983) *Proc. Natl. Acad. Sci. USA* 80, 4803).

The cell can include a nucleic acid of the invention which encodes a polypeptide, wherein the cells expresses a polypeptide of the invention. The cell can also include vector sequences, or the like. Furthermore, cells and transgenic plants which include any polypeptide or nucleic acid above or throughout this specification, e.g., produced by transduction of a vector of the invention, are an additional feature of the invention.

For long-term, high-yield production of recombinant proteins, stable expression can be used. Host cells transformed with a nucleotide sequence encoding a polypeptide of the invention are optionally cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding mature proteins of the invention can be designed with signal sequences which direct secretion of the mature polypeptides through a prokaryotic or eukaryotic cell membrane.

Identification of Additional Factors

A transcription factor provided by the present invention can also be used to identify additional endogenous or exogenous molecules that can affect a phentoype or trait of interest. On the one hand, such molecules include organic (small or large molecules) and/or inorganic compounds that affect expression of (i.e., regulate) a particular transcription factor. Alternatively, such molecules include endogenous molecules that are acted upon either at a transcriptional level by a transcription factor of the invention to modify a phenotype as desired. For example, the transcription factors can be employed to identify one or more downstream gene with which is subject to a regulatory effect of the transcription factor. In one approach, a transcription factor or transcription factor homologue of the invention is expressed in a host cell, e.g, a transgenic plant cell, tissue or explant, and expression products, either RNA or protein, of likely or random targets are monitored, e.g., by hybridization to a microarray of nucleic acid probes corresponding to genes expressed in a tissue or cell type of interest, by two-dimensional gel electrophoresis of protein products, or by any other method known in the art for assessing expression of gene products at the level of RNA or protein. Alternatively, a transcription factor of the invention can be used to identify promoter sequences (i.e., binding sites) involved in the regulation of a downstream target. After identifying a promoter sequence, interactions between the transcription factor and the promoter sequence can be modified by changing specific nucleotides in the promoter sequence or specific amino acids in the transcription factor that interact with the promoter sequence to alter a plant trait. Typically, transcription factor DNA binding sites are identified by gel shift assays. After identifying the promoter regions, the promoter region sequences can be employed in double-stranded DNA arrays to identify molecules that affect the interactions of the transcription factors with their promoters (Bulyk et al. (1999) *Nature Biotechnology* 17:573–577).

The identified transcription factors are also useful to identify proteins that modify the activity of the transcription factor. Such modification can occur by covalent modification, such as by phosphorylation, or by protein-protein (homo or-heteropolymer) interactions. Any method suitable for detecting protein-protein interactions can be employed. Among the methods that can be employed are coimmunoprecipitation, cross-linking and co-purification through gradients or chromatographic columns, and the two-hybrid yeast system.

The two-hybrid system detects protein interactions in vivo and is described in Chien, et al., (1991), *Proc. Natl. Acad. Sci. USA* 88, 9578–9582 and is commercially available from Clontech (Palo Alto, Calif.). In such a system, plasmids are constructed that encode two hybrid proteins: one consists of the DNA-binding domain of a transcription activator protein fused to the TF polypeptide and the other consists of the transcription activator protein's activation domain fused to an unknown protein that is encoded by a cDNA that has been recombined into the plasmid as part of a cDNA library. The DNA-binding domain fusion plasmid and the cDNA library are transformed into a strain of the yeast *Saccharomyces cerevisiae* that contains a reporter gene (e.g., lacZ) whose regulatory region contains the transcription activator's binding site. Either hybrid protein alone cannot activate transcription of the reporter gene. Interaction of the two hybrid proteins reconstitutes the functional activator protein and results in expression of the reporter gene, which is detected by an assay for the reporter gene product. Then, the library plasmids responsible for reporter gene expression are isolated and sequenced to identify the proteins encoded by the library plasmids. After identifying proteins that interact with the transcription factors, assays for compounds that interfere with the TF protein-protein interactions can be preformed.

Identification of Modulators

In addition to the intracellular molecules described above, extracellular molecules that alter activity or expression of a transcription factor, either directly or indirectly, can be identified. For example, the methods can entail first placing a candidate molecule in contact with a plant or plant cell. The molecule can be introduced by topical administration, such as spraying or soaking of a plant, and then the molecule's effect on the expression or activity of the TF polypeptide or the expression of the polynucleotide monitored. Changes in the expression of the TF polypeptide can be monitored by use of polyclonal or monoclonal antibodies, gel electrophoresis or the like. Changes in the expression of the corresponding polynucleotide sequence can be detected by use of microarrays, Northerns, quantitative PCR, or any other technique for monitoring changes in mRNA expression. These techniques are exemplified in Ausubel et al. (eds) *Current Protocols in Molecular Biology,* John Wiley & Sons (1998). Such changes in the expression levels can be correlated with modified plant traits and thus identified molecules can be useful for soaking or spraying on fruit, vegetable and grain crops to modify traits in plants.

Essentially any available composition can be tested for modulatory activity of expression or activity of any nucleic acid or polypeptide herein. Thus, available libraries of compounds such as chemicals, polypeptides, nucleic acids and the like can be tested for modulatory activity. Often, potential modulator compounds can be dissolved in aqueous or organic (e.g., DMSO-based) solutions for easy delivery to the cell or plant of interest in which the activity of the modulator is to be tested. Optionally, the assays are designed to screen large modulator composition libraries by automating the assay steps and providing compounds from any convenient source to assays, which are typically run in parallel (e.g., in microtiter formats on microtiter plates in robotic assays).

In one embodiment, high throughput screening methods involve providing a combinatorial library containing a large number of potential compounds (potential modulator compounds). Such "combinatorial chemical libraries" are then screened in one or more assays, as described herein, to identify those library members (particular chemical species or subclasses) that display a desired characteristic activity. The compounds thus identified can serve as target compounds.

A combinatorial chemical library can be, e.g., a collection of diverse chemical compounds generated by chemical synthesis or biological synthesis. For example, a combinatorial chemical library such as a polypeptide library is formed by combining a set of chemical building blocks (e.g., in one example, amino acids) in every possible way for a given compound length (i.e., the number of amino acids in a polypeptide compound of a set length). Exemplary libraries include peptide libraries, nucleic acid libraries, antibody libraries (see, e.g., Vaughn et al. (1996) *Nature Biotechnology,* 14(3):309–314 and PCT/US96/110287), carbohydrate libraries (see, e.g., Liang et al. *Science* (1996) 274:1520–1522 and U.S. Pat. No. 5,593,853), peptide nucleic acid libraries (see, e.g., U.S. Pat. No. 5,539,083), and small organic molecule libraries (see, e.g., benzodiazepines, Baum *C&EN* Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337) and the like.

Preparation and screening of combinatorial or other libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al. *Nature* 354:84–88 (1991)). Other chemistries for generating chemical diversity libraries can also be used.

In addition, as noted, compound screening equipment for high-throughput screening is generally available, e.g., using any of a number of well known robotic systems that have also been developed for solution phase chemistries useful in assay systems. These systems include automated workstations including an automated synthesis apparatus and robotic systems utilizing robotic arms. Any of the above devices are suitable for use with the present invention, e.g., for high-throughput screening of potential modulators. The nature and implementation of modifications to these devices (if any) so that they can operate as discussed herein will be apparent to persons skilled in the relevant art.

Indeed, entire high throughput screening systems are commercially available. These systems typically automate entire procedures including all sample and reagent pipetting, liquid dispensing, timed incubations, and fmal readings of the microplate in detector(s) appropriate for the assay. These configurable systems provide high throughput and rapid start up as well as a high degree of flexibility and customization. Similarly, microfluidic implementations of screening are also commercially available.

The manufacturers of such systems provide detailed protocols the various high throughput. Thus, for example, Zymark Corp. provides technical bulletins describing screening systems for detecting the modulation of gene transcription, ligand binding, and the like. The integrated systems herein, in addition to providing for sequence alignment and, optionally, synthesis of relevant nucleic acids, can include such screening apparatus to identify modulators that have an effect on one or more polynucleotides or polypeptides according to the present invention.

In some assays it is desirable to have positive controls to ensure that the components of the assays are working properly. At least two types of positive controls are appropriate. That is, known transcriptional activators or inhibitors can be incubated with cells/plants/etc. in one sample of the assay, and the resulting increase/decrease in transcription can be detected by measuring the resulting increase in RNA/protein expression, etc., according to the methods herein. It will be appreciated that modulators can also be combined with transcriptional activators or inhibitors to find modulators which inhibit transcriptional activation or transcriptional repression. Either expression of the nucleic acids and proteins herein or any additional nucleic acids or proteins activated by the nucleic acids or proteins herein, or both, can be monitored.

In an embodiment, the invention provides a method for identifying compositions that modulate the activity or expression of a polynucleotide or polypeptide of the invention. For example, a test compound, whether a small or large molecule, is placed in contact with a cell, plant (or plant tissue or explant), or composition comprising the polynucleotide or polypeptide of interest and a resulting effect on the cell, plant, (or tissue or explant) or composition is evaluated by monitoring, either directly or indirectly, one or more of: expression level of the polynucleotide or polypeptide, activity (or modulation of the activity) of the polynucleotide or polypeptide. In some cases, an alteration in a plant phenotype can be detected following contact of a plant (or plant cell, or tissue or explant) with the putative modulator, e.g., by modulation of expression or activity of a polynucleotide or polypeptide of the invention.

Subsequences

Also contemplated are uses of polynucleotides, also referred to herein as oligonucleotides, typically having at least 12 bases, preferably at least 15, more preferably at least 20, 30, or 50 bases, which hybridize under at least highly stringent (or ultra-high stringent or ultra-ultra-high stringent conditions) conditions to a polynucleotide sequence described above. The polynucleotides may be used as probes, primers, sense and antisense agents, and the like, according to methods as noted supra.

Subsequences of the polynucleotides of the invention, including polynucleotide fragments and oligonucleotides are useful as nucleic acid probes and primers. An oligonucleotide suitable for use as a probe or primer is at least about 15 nucleotides in length, more often at least about 18 nucleotides, often at least about 21 nucleotides, frequently at least about 30 nucleotides, or about 40 nucleotides, or more in length. A nucleic acid probe is useful in hybridization protocols, e.g., to identify additional polypeptide homologues of the invention, including protocols for microarray experiments. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods. See Sambrook and Ausubel, supra.

In addition, the invention includes an isolated or recombinant polypeptide including a subsequence of at least about 15 contiguous amino acids encoded by the recombinant or isolated polynucleotides of the invention. For example, such polypeptides, or domains or fragments thereof, can be used as immunogens, e.g., to produce antibodies specific for the polypeptide sequence, or as probes for detecting a sequence of interest. A subsequence can range in size from about 15 amino acids in length up to and including the full length of the polypeptide.

Production of Transgenic Plants

Modification of Traits

The polynucleotides of the invention are favorably employed to produce transgenic plants with various traits, or characteristics, that have been modified in a desirable manner, e.g., to improve plant biomass. For example, alteration of expression levels or patterns (e.g., spatial or temporal expression patterns) of one or more of the transcription factors (or transcription factor homologues) of the invention, as compared with the levels of the same protein found in a wild type plant, can be used to modify a plant's traits. An illustrative example of trait modification, improved plant biomass, by altering expression levels of a particular transcription factor is described further in the Examples and the Sequence Listing.

Antisense and Cosuppression Approaches

In addition to expression of the nucleic acids of the invention as gene replacement or plant phenotype modification nucleic acids, the nucleic acids are also useful for sense and anti-sense suppression of expression, e.g., to down-regulate expression of a nucleic acid of the invention, e.g., as a further mechanism for modulating plant phenotype. That is, the nucleic acids of the invention, or subsequences or anti-sense sequences thereof, can be used to block expression of naturally occurring homologous nucleic acids. A variety of sense and anti-sense technologies are known in the art, e.g., as set forth in Lichtenstein and Nellen (1997) *Antisense Technology: A Practical Approach* IRL Press at Oxford University, Oxford, England. In general, sense or anti-sense sequences are introduced into a cell, where they are optionally amplified, e.g., by transcription. Such sequences include both simple oligonucleotide sequences and catalytic sequences such as ribozymes.

For example, a reduction or elimination of expression (i.e., a "knock-out") of a transcription factor or transcription factor homologue polypeptide in a transgenic plant, e.g., to modify a plant trait, can be obtained by introducing an antisense construct corresponding to the polypeptide of interest as a cDNA. For antisense suppression, the transcription factor or homologue cDNA is arranged in reverse orientation (with respect to the coding sequence) relative to the promoter sequence in the expression vector. The introduced sequence need not be the full length cDNA or gene, and need not be identical to the cDNA or gene found in the plant type to be transformed. Typically, the antisense sequence need only be capable of hybridizing to the target gene or RNA of interest. Thus, where the introduced sequence is of shorter length, a higher degree of homology to the endogenous transcription factor sequence will be needed for effective antisense suppression. While antisense sequences of various lengths can be utilized, preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous transcription factor gene in the plant cell.

Suppression of endogenous transcription factor gene expression can also be achieved using a ribozyme. Ribozymes are RNA molecules that possess highly specific endoribonuclease activity. The production and use of ribozymes are disclosed in U.S. Pat. No. 4,987,071 and U.S. Pat. No. 5,543,508. Synthetic ribozyme sequences including antisense RNAs can be used to confer RNA cleaving activity on the antisense RNA, such that endogenous mRNA molecules that hybridize to the antisense RNA are cleaved, which in turn leads to an enhanced antisense inhibition of endogenous gene expression.

Vectors in which RNA encoded by a transcription factor or transcription factor homologue cDNA is over-expressed can also be used to obtain co-suppression of a corresponding endogenous gene, e.g., in the manner described in U.S. Pat. No. 5,231,020 to Jorgensen. Such co-suppression (also termed sense suppression) does not require that the entire transcription factor cDNA be introduced into the plant cells, nor does it require that the introduced sequence be exactly identical to the endogenous transcription factor gene of interest. However, as with antisense suppression, the suppressive efficiency will be enhanced as specificity of hybridization is increased, e.g., as the introduced sequence is lengthened, and/or as the sequence similarity between the introduced sequence and the endogenous transcription factor gene is increased.

Vectors expressing an untranslatable form of the transcription factor mRNA, e.g., sequences comprising one or more stop codon, or nonsense mutation) can also be used to suppress expression of an endogenous transcription factor, thereby reducing or eliminating it's activity and modifying one or more traits. Methods for producing such constructs are described in U.S. Pat. No. 5,583,021. Preferably, such constructs are made by introducing a premature stop codon into the transcription factor gene. Alternatively, a plant trait can be modified by gene silencing using double-strand RNA (Sharp (1999) *Genes and Development* 13: 139–141).

Another method for abolishing the expression of a gene is by insertion mutagenesis using the T-DNA of *Agrobacterium tumefaciens*. After generating the insertion mutants, the mutants can be screened to identify those containing the insertion in a transcription factor or transcription factor homologue gene. Plants containing a single transgene insertion event at the desired gene can be crossed to generate homozygous plants for the mutation (Koncz et al. (1992) *Methods in Arabidopsis Research*, World Scientific).

Alternatively, a plant phenotype can be altered by eliminating an endogenous gene, such as a transcription factor or transcription factor homologue, e.g., by homologous recombination (Kempin et al. (1997) *Nature* 389:802).

A plant trait can also be modified by using the cre-lox system (for example, as described in U.S. Pat. No. 5,658,772). A plant genome can be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

The polynucleotides and polypeptides of this invention can also be expressed in a plant in the absence of an expression cassette by manipulating the activity or expression level of the endogenous gene by other means. For example, by ectopically expressing a gene by T-DNA activation tagging (Ichikawa et al. (1997) *Nature* 390 698–701; Kakimoto et al. (1996) *Science* 274: 982–985). This method entails transforming a plant with a gene tag containing multiple transcriptional enhancers and once the tag has inserted into the genome, expression of a flanking gene coding sequence becomes deregulated. In another example, the transcriptional machinery in a plant can be modified so as to increase transcription levels of a polynucleotide of the invention (See, e.g., PCT Publications WO 96/06166 and WO 98/53057 which describe the modification of the DNA binding specificity of zinc finger proteins by changing particular amino acids in the DNA binding motif).

The transgenic plant can also include the machinery necessary for expressing or altering the activity of a polypeptide encoded by an endogenous gene, for example by altering the phosphorylation state of the polypeptide to maintain it in an activated state.

Transgenic plants (or plant cells, or plant explants, or plant tissues) incorporating the polynucleotides of the invention and/or expressing the polypeptides of the invention can be produced by a variety of well established techniques as described above. Following construction of a vector, most typically an expression cassette, including a polynucleotide, e.g., encoding a transcription factor or transcription factor homologue, of the invention, standard techniques can be used to introduce the polynucleotide into a plant, a plant cell, a plant explant or a plant tissue of interest. Optionally, the plant cell, explant or tissue can be regenerated to produce a transgenic plant.

The plant can be any higher plant, including gymnosperms, monocotyledonous and dicotyledenous plants. Suitable protocols are available for Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops. See protocols described in Ammirato et al. (1984) *Handbook of Plant Cell Culture—crop Species*. Macmillan Publ. Co. Shimamoto et al. (1989) *Nature* 338:274–276; Fromm et al. (1990) *Bio/Technology* 8:833–839; and Vasil et al. (1990) *Bio/Technology* 8:429–434.

Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* mediated transformation. Transformation means introducing a nucleotide sequence in a plant in a manner to cause stable or transient expression of the sequence.

Successful examples of the modification of plant characteristics by transformation with cloned sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants are preferably selected using a dominant selectable marker incorporated into the transformation vector. Typically, such a marker will confer antibiotic or herbicide resistance on the transformed plants, and selection of transformants can be accomplished by exposing the plants to appropriate concentrations of the antibiotic or herbicide.

After transformed plants are selected and grown to maturity, those plants showing a modified trait are identified. The modfied trait can be any of those traits described above. Additionally, to confirm that the modified trait is due to changes in expression levels or activity of the polypeptide or polynucleotide of the invention can be determined by analyzing mRNA expression using Northern blots, RT-PCR or microarrays, or protein expression using immunoblots or Western blots or gel shift assays.

Integrated Systems—Sequence Identity

Additionally, the present invention may be an integrated system, computer or computer readable medium that comprises an instruction set for determining the identity of one or more sequences in a database. In addition, the instruction set can be used to generate or identify sequences that meet any specified criteria. Furthermore, the instruction set may be used to associate or link certain functional benefits, such as an improved plant biomass, with one or more identified sequence.

For example, the instruction set can include, e.g., a sequence comparison or other alignment program, e.g., an available program such as, for example, the Wisconsin Package Version 10.0, such as BLAST, FASTA, PILEUP, FINDPATTERNS or the like (GCG, Madision, Wis.). Public sequence databases such as GenBank, EMBL, Swiss-Prot and PIR or private sequence databases such as PhytoSeq (Incyte Pharmaceuticals, Palo Alto, Calif.) can be searched.

Alignment of sequences for comparison can be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci. U.S.A.* 85: 2444, by computerized implementations of these algorithms. After alignment, sequence comparisons between two (or more) polynucleotides or polypeptides are typically performed by comparing sequences of the two sequences over a comparison window to identify and compare local regions of sequence similarity. The comparison window can be a segment of at least about 20 contiguous positions, usually about 50 to about 200, more usually about 100 to about 150 contiguous positions. A description of the method is provided in Ausubel et al., supra.

A variety of methods of determining sequence relationships can be used, including manual alignment and computer assisted sequence alignment and analysis. This later approach is a preferred approach in the present invention, due to the increased throughput afforded by computer assisted methods. As noted above, a variety of computer programs for performing sequence alignment are available, or can be produced by one of skill.

One example algorithm that is suitable for determining percent sequence identity and sequence similarity is the BLAST algorithm, which is described in Altschul et al. *J. Mol. Biol* 215:403–410 (1990). Software for performing BLAST analyses is publicly available, e.g., through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Natl. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, in this context, homologous) if the smallest sum probability in a comparison of the test nucleic acid to the reference nucleic acid is less than about 0.1, or less than about 0.01, and or even less than about 0.001. An additional example of a useful sequence alignment algorithm is PILEUP. PILEUP creates a multiple sequence alignment from a group of related sequences using progressive, pairwise aligmnents. The program can align, e.g., up to 300 sequences of a maximum length of 5,000 letters.

The integrated system, or computer typically includes a user input interface allowing a user to selectively view one or more sequence records corresponding to the one or more character strings, as well as an instruction set which aligns the one or more character strings with each other or with an additional character string to identify one or more region of sequence similarity. The system may include a link of one or more character strings with a particular phenotype or gene function. Typically, the system includes a user readable output element which displays an alignment produced by the alignment instruction set.

The methods of this invention can be implemented in a localized or distributed computing environment. In a distributed environment, the methods may implemented on a single computer comprising multiple processors or on a multiplicity of computers. The computers can be linked, e.g. through a common bus, but more preferably the computer(s) are nodes on a network. The network can be a generalized or a dedicated local or wide-area network and, in certain preferred embodiments, the computers may be components of an intra-net or an internet.

Thus, the invention provides methods for identifying a sequence similar or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an inter or intra net) and a query is made against the sequence database using the relevant sequences herein and associated plant phenotypes or gene functions.

Any sequence herein can be entered into the database, before or after querying the database. This provides for both expansion of the database and, if done before the querying step, for insertion of control sequences into the database. The control sequences can be detected by the query to ensure the general integrity of both the database and the query. As noted, the query can be performed using a web browser based interface. For example, the database can be a centralized public database such as those noted herein, and the querying can be done from a remote terminal or computer across an internet or intranet.

EXAMPLES

The following examples are intended to illustrate but not limit the present invention.

Example I

Full Length Gene Identification and Cloning

Putative transcription factor sequences (genomic or ESTs) related to known transcription factors were identified in the *Arabidopsis thaliana* GenBank database using the tblastn sequence analysis program using default parameters and a P-value cutoff threshold of −4 or −5 or lower, depending on the length of the query sequence. Putative transcription factor sequence hits were then screened to identify those containing particular sequence strings. If the sequence hits contained such sequence strings, the sequences were confirmed as transcription factors.

Alternatively, *Arabidopsis thaliana* cDNA libraries derived from different tissues or treatments, or genomic libraries were screened to identify novel members of a transcription family using a low stringency hybridization approach. Probes were synthesized using gene specific primers in a standard PCR reaction (annealing temperature 60° C.) and labeled with $^{32}P$ dCTP using the High Prime DNA Labeling Kit (Boehringer Mannheim). Purified radiolabelled probes were added to filters immersed in Church hybridization medium (0.5 M $NaPO_4$ pH 7.0, 7% SDS, 1% w/v bovine serum albumin) and hybridized overnight at 60° C. with shaking. Filters were washed two times for 45 to 60 minutes with 1×SCC, 1% SDS at 60° C.

To identify additional sequence 5' or 3' of a partial cDNA sequence in a cDNA library, 5' and 3' rapid amplification of cDNA ends (RACE) was performed using the Marathon™ cDNA amplification kit (Clontech, Palo Alto, Calif.). Generally, the method entailed first isolating poly(A) mRNA, performing first and second strand cDNA synthesis to generate double stranded cDNA, blunting cDNA ends, followed by ligation of the Marathon™ Adaptor to the cDNA to form a library of adaptor-ligated ds cDNA.

Gene-specific primers were designed to be used along with adaptor specific primers for both 5' and 3' RACE reactions. Nested primers, rather than single primers, were used to increase PCR specificity. Using 5' and 3' RACE reactions, 5' and 3' RACE fragments were obtained, sequenced and cloned. The process can be repeated until 5' and 3' ends of the full-length gene were identified. Then the full-length cDNA was generated by PCR using primers specific to 5' and 3' ends of the gene by end-to-end PCR.

Example II

Construction of Expression Vectors

The sequence was amplified from a genomic or cDNA library using primers specific to sequences upstream and downstream of the coding region. The expression vector was pMEN20 or pMEN65, which are both derived from pMON316 (Sanders et al, (1987) *Nucleic Acids Research* 15:1543–58) and contain the CaMV 35S promoter to express transgenes. To clone the sequence into the vector, both pMEN20 and the amplified DNA fragment were digested separately with SalI and NotI restriction enzymes at 37° C. for 2 hours. The digestion products were subject to electrophoresis in a 0.8% agarose gel and visualized by ethidium bromide staining. The DNA fragments containing the sequence and the linearized plasmid were excised and purified by using a Qiaquick gel extraction kit (Qiagen, Calif.). The fragments of interest were ligated at a ratio of 3:1 (vector to insert). Ligation reactions using T4 DNA ligase (New England Biolabs, Mass.) were carried out at 16° C. for 16 hours. The ligated DNAs were transformed into competent cells of the *E. coli* strain DH5alpha by using the heat shock method. The transformations were plated on LB plates containing 50 mg/l kanamycin (Sigma).

Individual colonies were grown overnight in five milliliters of LB broth containing 50 mg/l kanamycin at 37° C. Plasmid DNA was purified by using Qiaquick Mini Prep kits (Qiagen, Calif.).

Example III

Transformation of Agrobacterium with the Expression Vector

After the plasmid vector containing the gene was constructed, the vector was used to transform *Agrobacterium tumefaciens* cells expressing the gene products. The stock of *Agrobacterium tumefaciens* cells for transformation were made as described by Nagel et al. (1990) *FEMS Microbiol Letts.* 67: 325–328. Agrobacterium strain ABI was grown in 250 ml LB medium (Sigma) overnight at 28° C. with shaking until an absorbance ($A_{600}$) of 0.5–1.0 was reached. Cells were harvested by centrifugation at 4,000× g for 15 min at 4° C. Cells were then resuspended in 250 µl chilled buffer (1 mM HEPES, pH adjusted to 7.0 with KOH). Cells were centrifuged again as described above and resuspended in 125 µl chilled buffer. Cells were then centrifuged and resuspended two more times in the same HEPES buffer as described above at a volume of 100 µl and 750 µl, respectively. Resuspended cells were then distributed into 40 µl aliquots, quickly frozen in liquid nitrogen, and stored at −80° C.

Agrobacterium cells were transformed with plasmids prepared as described above following the protocol described by Nagel et al. For each DNA construct to be transformed, 50–100 ng DNA (generally resuspended in 10 mM Tris-HCl, 1 mM EDTA, pH 8.0) was mixed with 40 µl of Agrobacterium cells. The DNA/cell mixture was then transferred to a chilled cuvette with a 2 mm electrode gap and subject to a 2.5 kV charge dissipated at 25 µF and 200 µF using a Gene Pulser II apparatus (Bio-Rad). After electroporation, cells were immediately resuspended in 1.0 ml LB and allowed to recover without antibiotic selection for 2–4 hours at 28° C. in a shaking incubator. After recovery, cells were plated onto selective medium of LB broth containing 100 µg/ml spectinomycin (Sigma) and incubated for 24–48 hours at 28° C. Single colonies were then picked and inoculated in fresh medium. The presence of the plasmid construct was verified by PCR amplification and sequence analysis.

Example IV

Transformation of Arabidopsis Plants with *Agrobacterium Tumefaciens* with Expression Vector After transformation of *Agrobacterium tumefaciens* with plasmid vectors containing the gene, single Agrobacterium colonies were identified, propagated, and used to transform Arabidopsis plants. Briefly, 500 ml cultures of LB medium containing 50 mg/l kanamycin were inoculated with the colonies and grown at 28° C. with shaking for 2 days until an absorbance ($A_{600}$) of >2.0 is reached. Cells were then harvested by centrifugation at 4,000 × g for 10 min, and resuspended in infiltration medium (½ X Murashige and Skoog salts (Sigma), 1 X Gamborg's B-5 vitamins (Sigma), 5.0% (w/v) sucrose (Sigma), 0.044 µM benzylamino purine (Sigma), 200 µl/L Silwet L-77 (Lehle Seeds) until an absorbance ($A_{600}$) of 0.8 was reached.

Prior to transformation, *Arabidopsis thaliana* seeds (ecotype Columbia) were sown at a density of ~10 plants per 4" pot onto Pro-Mix BX potting medium (Hummert International) covered with fiberglass mesh (18 mm×16 mm). Plants were grown under continuous illumination (50–75 µE/m²/sec) at 22–23° C. with 65–70% relative humidity. After about 4 weeks, primary inflorescence stems (bolts) are cut off to encourage growth of multiple secondary bolts. After flowering of the mature secondary bolts, plants were prepared for transformation by removal of all siliques and opened flowers.

The pots were then immersed upside down in the mixture of Agrobacterium infiltration medium as described above for 30 sec, and placed on their sides to allow draining into a 1'×2' flat surface covered with plastic wrap. After 24 h, the plastic wrap was removed and pots are turned upright. The immersion procedure was repeated one week later, for a total of two immersions per pot. Seeds were then collected from each transformation pot and analyzed following the protocol described below.

Example V

Identification of Arabidopsis Primary Transformants

Seeds collected from the transformation pots were sterilized essentially as follows. Seeds were dispersed into in a solution containing 0.1% (v/v) Triton X-100 (Sigma) and sterile $H_2O$ and washed by shaking the suspension for 20 min. The wash solution was then drained and replaced with fresh wash solution to wash the seeds for 20 min with shaking. After removal of the second wash solution, a solution containing 0.1% (v/v) Triton X-100 and 70% ethanol (Equistar) was added to the seeds and the suspension was shaken for 5 min. After removal of the ethanol/detergent solution, a solution containing 0.1% (v/v) Triton X-100 and 30% (v/v) bleach (Clorox) was added to the seeds, and the suspension was shaken for 10 min. After removal of the bleach/detergent solution, seeds were then washed five times in sterile distilled $H_2O$. The seeds were stored in the last wash water at 4° C. for 2 days in the dark before being plated onto antibiotic selection medium (1 × Murashige and Skoog salts (pH adjusted to 5.7 with 1M KOH), 1 × Gamborg's B-5 vitamins, 0.9% phytagar (Life Technologies), and 50 mg/l kanamycin). Seeds were germinated under continuous illumination (50–75 $\mu E/m^2$/sec) at 22–23° C. After 7–10 days of growth under these conditions, kanamycin resistant primary transformants ($T_1$ generation) were visible and obtained. These seedlings were transferred first to fresh selection plates where the seedlings continued to grow for 3–5 more days, and then to soil (Pro-Mix BX potting medium).

Primary transformants were crossed and progeny seeds ($T_2$) collected; kanamycin resistant seedlings were selected and analyzed. The expression levels of the recombinant polynucleotides in the transformants varies from about a 5% expression level increase to a least a 100% expression level increase. Similar observations are made with respect to polypeptide level expression.

Example VI

Identification of Arabidopsis Plants with Transcription Factor Gene Knockouts

The screening of insertion mutagenized Arabidopsis collections for null mutants in a known target gene was essentially as described in Krysan et al (1999) *Plant Cell* 11:2283–2290. Briefly, gene-specific primers, nested by 5–250 base pairs to each other, were designed from the 5' and 3' regions of a known target gene. Similarly, nested sets of primers were also created specific to each of the T-DNA or transposon ends (the "right" and "left" borders). All possible combinations of gene specific and T-DNA/transposon primers were used to detect by PCR an insertion event within or close to the target gene. The amplified DNA fragments were then sequenced which allows the precise determination of the T-DNA/transposon insertion point relative to the target gene. Insertion events within the coding or intervening sequence of the genes were deconvoluted from a pool comprising a plurality of insertion events to a single unique mutant plant for functional characterization. The method is described in more detail in Yu and Adam, U.S. application Ser. No. 09/177,733 filed Oct. 23, 1998.

Example VII

Identification of Overexpressor or Gene Knockout Plants With Modified Plant Biomass Experiments were performed to identify those transformants or knockouts that exhibited a modified biomass phenotype. The plants were grown under continuous light conditions at 20–25° C. For such studies, the transformants leaves and seeds were observed for a modified phenotype. For plant dry weight determination, a plant was place in an oven for 3 days at 65 to 70° C.

We observed that plants overexpressing G1073 (SEQ ID Nos. 1 and 2) constitutively (three independent T2 populations having 6 plants in one population and 16 plants in each of the other two) had increased biomass as measured by an increase in the plant fresh weight, the plant's dry weight or the seed yield compared with control plants transformed with an empty transformation vector under the control of the 35S promoter. Typically, the plant fresh weight, dry weight or seed yield were increased by at least 150%.

We identified additional genes that are related to G1073 based on sequence identity and therefore are suitable for increasing plant biomass. The genes were G2789 (SEQ ID Nos: 3 and 4), G1945 (SEQ ID Nos. 5 and 6), and G2155 (SEQ ID Nos 7 and 8). G2789 shares 89% sequence identity over a conserved domain of G1073 (amino acid residues 33 through 50 of SEQ ID No. 2), whereas G1945 shares about an 89% sequence identity over the same domain and G2155 shares a 78% sequence identity over that domain. G2155 and G1945 share an 83% sequence identity over that region. To confirm that these related transcription factors could be used to modify plant biomass, we measured changes in plant biomass for G2155 or G2789 overexpressors. We observed that when either G2155 or G2789 were overexpressed in plants the transformed plants were substantially larger than the wild type plant.

All references, publications, patents and other documents herein are incorporated by reference in their entirety for all purposes. Although the invention has been described with reference to the embodiments and examples above, it should be understood that various modifications can be made without departing from the spirit of the invention.

What is claimed is:

1. A transgenic plant comprising a recombinant polynucleotide comprising:
   (a) a nucleotide sequence encoding a polypeptide comprising SEQ ID NO: 2, or a sequence that is fully complementary to the nucleotide sequence encoding a polypeptide comprising SEQ ID NO; 2; or
   (b) a nucleotide sequence comprising SEQ ID NO: 1, or a sequence that is fully complementary to the nucleotide sequence comprising SEQ ID NO: 1;
   wherein expression of the recombinant polynucleotide comprising either (a) or (b) increases the plant's biomass as compared to a control plant not transformed with said recombinant polynucleotide.

2. The transgenic plant of claim 1, further comprising a constitutive, inducible, or tissue-active promoter operably linked to the nucleotide sequence comprising any of (a)–(i).

3. A transgenic plant comprising a recombinant polynucleotide comprising a polynucleotide sequence that hybridizes over its full length under stringent conditions to:
   (a) a nucleotide sequence comprising SEQ ID NO: 1, or a sequence that is fully complementary to the nucleotide sequence comprising SEQ ID NO: 1; or
   (b) a nucleotide sequence encoding a polypeptide comprising SEQ ID NO: 2, or a sequence that is fully complementary to the nucleotide sequence encoding a polypeptide comprising SEQ ID NO: 2;
   wherein the stringent conditions comprise wash conditions of 0.2×SSC to 2.0×SSC, 0.1% SDS at 60–65° C. and wherein expression of the polynucleotide sequence that hybridizes to either (a) or (b) increases the plant's biomass as compared to a control plant not transformed with said recombinant polynucleotide.

4. The transgenic plant of claim 3, further comprising a constitutive, inducible, or tissue-active promoter operably linked to the polynucleotide sequence.

5. A method for producing a plant having increased biomass; said method comprising:
   (a) providing an expression vector or cassette comprising a polynucleotide sequence selected from the group consisting of:
      (i) a nucleotide sequence encoding a polypeptide comprising SEQ ID NO: 2 or a sequence that is fully complementary to the nucleotide sequence encoding a polypeptide comprising SEQ ID NO: 2;
      (ii) a nucleotide sequence comprising SEQ ID NO: 1 or a sequence that is fully complementary to the nucleotide sequence comprising SEQ ID NO: 1; and
      (iii) a nucleotide sequence that hybridizes under stringent conditions to a nucleotide sequence of (i) or (ii), wherein the stringent conditions comprise wash conditions of 0.2×SSC to 2.0×SSC, 0.1% SDS at 60–65° C.; wherein expression of the nucleotide sequence of (iii) increases the plant's biomass as compared to a control plant not transformed with said expression vector or cassette; and
   (b) transforming a plant with the expression vector or cassette, thereby producing a plant that expresses the nucleotide sequence of (i), (ii) or (iii), said plant having increased plant biomass as compared to a control plant not transformed with the expression vector or cassette.

6. A transgenic plant comprising a recombinant polynucleotide comprising a polynucleotide sequence that hybridizes over its full length under stringent conditions to:
   (a) a nucleotide sequence comprising SEQ ID NO: 1, or a sequence that is fully complementary to the nucleotide sequence comprising SEQ ID NO: 1; or
   (b) a nucleotide sequence encoding a polypeptide comprising SEQ ID NO: 2, or a sequence that is fully complementary to the nucleotide sequence encoding a polypeptide comprising SEQ ID NO: 2;
   wherein the stringent conditions comprise wash conditions of 0.2×SSC, 0.1% SDS at 65° C., and wherein expression of the polynucleotide sequence that hybridizes to either (a) or (b) increases the plant's biomass as compared to a control plant not transformed with said recombinant polynucleotide.

7. A method for producing a plant having increased biomass; said method comprising:
   (a) providing an expression vector or cassette comprising a polynucleotide sequence selected from the group consisting of:
      (i) a nucleotide sequence encoding a polypeptide comprising SEQ ID NO: 2 or a sequence that is fully complementary to the nucleotide sequence encoding a polypeptide comprising SEQ ID NO: 2;
      (ii) a nucleotide sequence comprising SEQ ID NO: 1 or a sequence that is fully complementary to the nucleotide sequence comprising SEQ ID NO: 1; and
      (iii) a nucleotide sequence that hybridizes under stringent conditions to a nucleotide sequence of (i) or (ii), wherein the stringent conditions comprise wash conditions of 0.2×SSC, 0.1% SDS, at 65° C.; wherein expression of the nucleotide sequence of (iii) increases the plant's biomass as compared to a control plant not transformed with said expression vector or cassette; and
   (b) transforming a plant with the expression vector or cassette, thereby producing a plant that expresses the nucleotide sequence of(i), (ii) or (iii), said plant having increased plant biomass as compared to a control plant not transformed with the expression vector or cassette.

\* \* \* \* \*